(12) United States Patent
Simpson et al.

(10) Patent No.: US 6,752,804 B2
(45) Date of Patent: Jun. 22, 2004

(54) ABLATION SYSTEM AND METHOD HAVING MULTIPLE-SENSOR ELECTRODES TO ASSIST IN ASSESSMENT OF ELECTRODE AND SENSOR POSITION AND ADJUSTMENT OF ENERGY LEVELS

(75) Inventors: John A. Simpson, Carlsbad, CA (US); Marshall L. Sherman, Cardiff, CA (US); David S. Wood, Temecula, CA (US); Jeffrey A. Hall, Birmingham, AL (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 424 days.

(21) Appl. No.: 09/752,782

(22) Filed: Dec. 28, 2000

(65) Prior Publication Data

US 2002/0128643 A1 Sep. 12, 2002

(51) Int. Cl.[7] .............................................. A61B 18/04
(52) U.S. Cl. ......................................... 606/34; 219/494
(58) Field of Search ............................... 606/34, 35, 36, 606/37, 38, 39, 40, 32, 41; 219/234, 482, 483, 484, 485, 486, 489, 490, 494, 497; 604/512

(56) References Cited

U.S. PATENT DOCUMENTS

| | | |
|---|---|---|
| 5,122,137 A | 6/1992 | Lennox |
| 5,233,515 A | 8/1993 | Cosman |
| 5,423,808 A | 6/1995 | Edwards et al. |
| 5,433,740 A | 7/1995 | Yamaguchi |
| 5,496,312 A | 3/1996 | Klicek |
| 5,540,681 A | 7/1996 | Strul et al. |
| 5,540,684 A | 7/1996 | Hassler, Jr. |
| 5,562,720 A | 10/1996 | Stern et al. |
| 5,573,533 A | 11/1996 | Strul |
| 5,584,830 A | 12/1996 | Ladd et al. |
| 5,769,847 A | 6/1998 | Panescu et al. |
| 5,810,802 A | 9/1998 | Panescu et al. |
| 5,837,001 A | 11/1998 | Mackey |
| 5,954,719 A | 9/1999 | Chen et al. |
| 5,971,980 A * | 10/1999 | Sherman ...................... 606/34 |
| 6,080,149 A | 6/2000 | Huang et al. |
| 6,123,702 A | 9/2000 | Swanson et al. |
| 6,162,217 A | 12/2000 | Kannenberg et al. |
| 6,183,468 B1 | 2/2001 | Swanson et al. |
| 6,350,263 B1 * | 2/2002 | Wetzig et al. ................ 606/41 |
| 6,358,245 B1 * | 3/2002 | Edwards et al. .............. 606/34 |
| 6,488,679 B1 * | 12/2002 | Swanson et al. .............. 606/40 |
| 6,511,478 B1 * | 1/2003 | Burnside et al. .............. 606/41 |

* cited by examiner

Primary Examiner—Daniel Robinson
(74) Attorney, Agent, or Firm—Fulwider Patton Lee & Utecht, LLP

(57) ABSTRACT

A catheter carries a plurality of electrodes, each with multiple thermal sensors attached and is used to position the electrodes proximal biological tissue. A processor responsive to each of the thermal sensors determines the temperature at the thermal-sensor/electrode junction. A display provides a graphic representation of the temperatures of the thermal-sensor/electrode junctions. An exemplary representation is a bar graph having the temperature of one thermal sensor at one end and the temperature of another thermal sensor at the other end. The length of the bar graph combined with the position of the bar graph relative to a temperature range region provides an indication of the position of the thermal-sensor/electrode junctions relative to the biological tissue. The processor also monitors the spread between the sensor temperatures and compares it to a threshold value. Base on the result of the comparison, the processor controls the power applied to the electrode.

13 Claims, 19 Drawing Sheets

FIG. 4
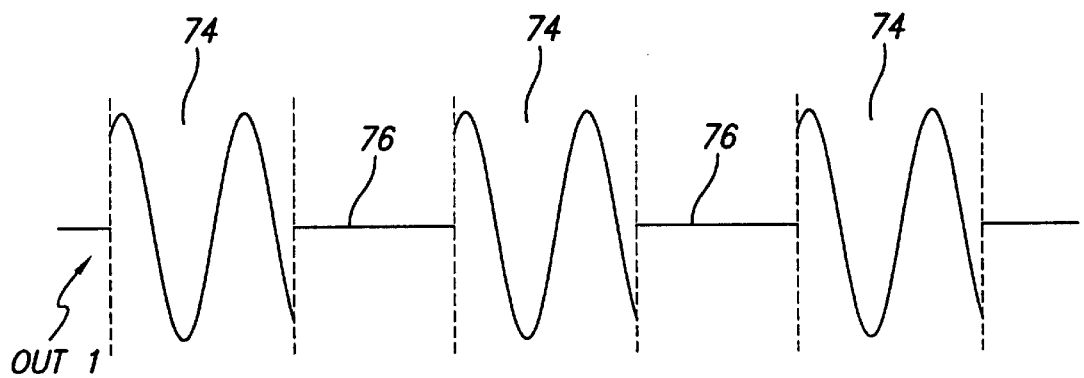
FIG. 5
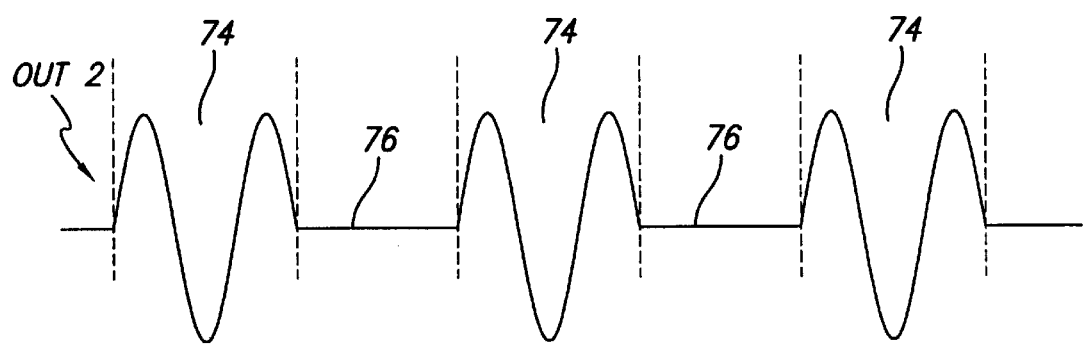
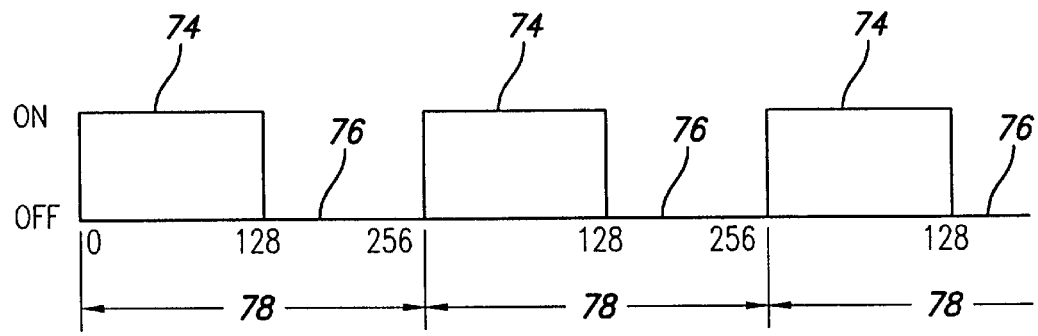
FIG. 6

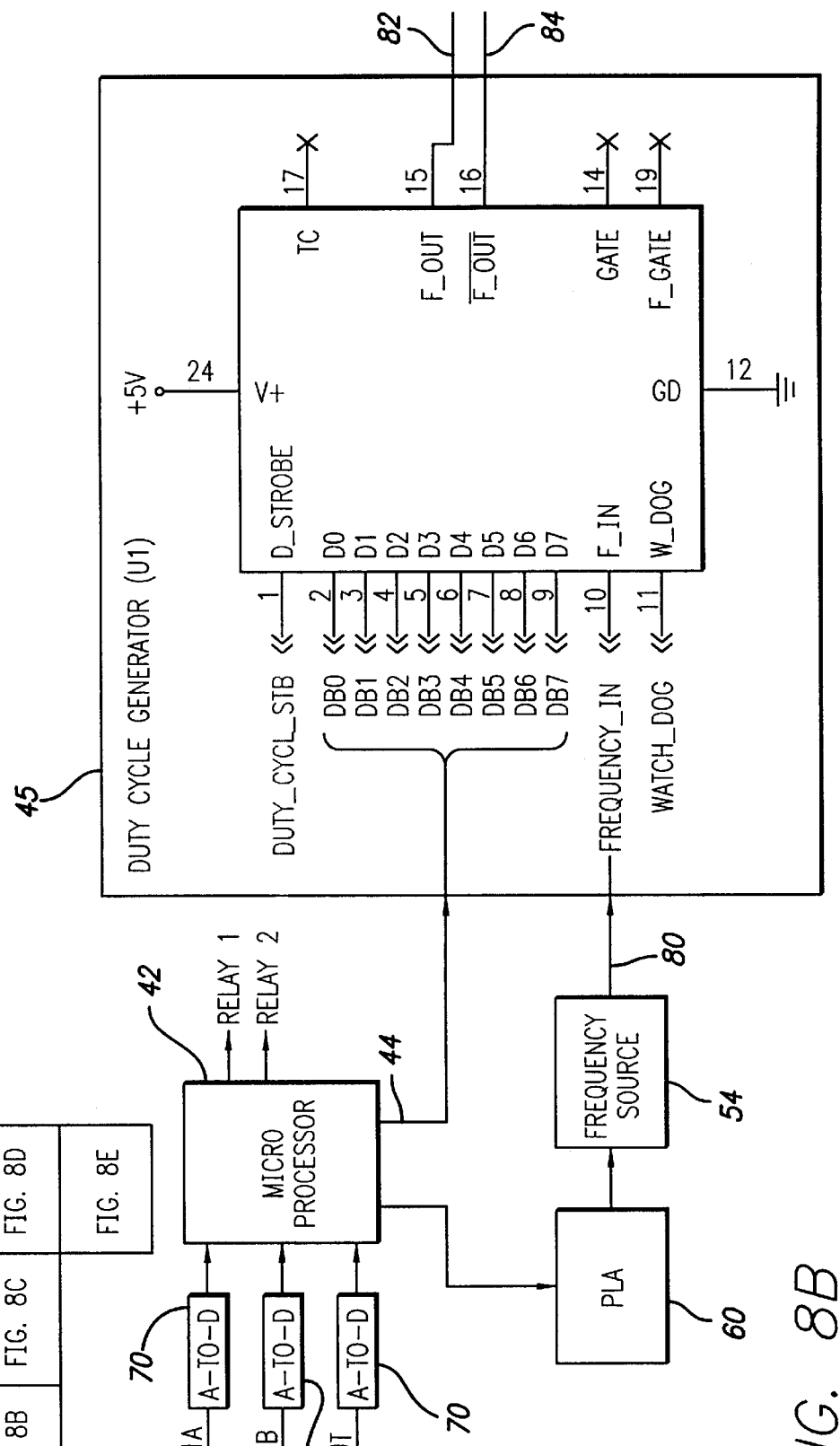

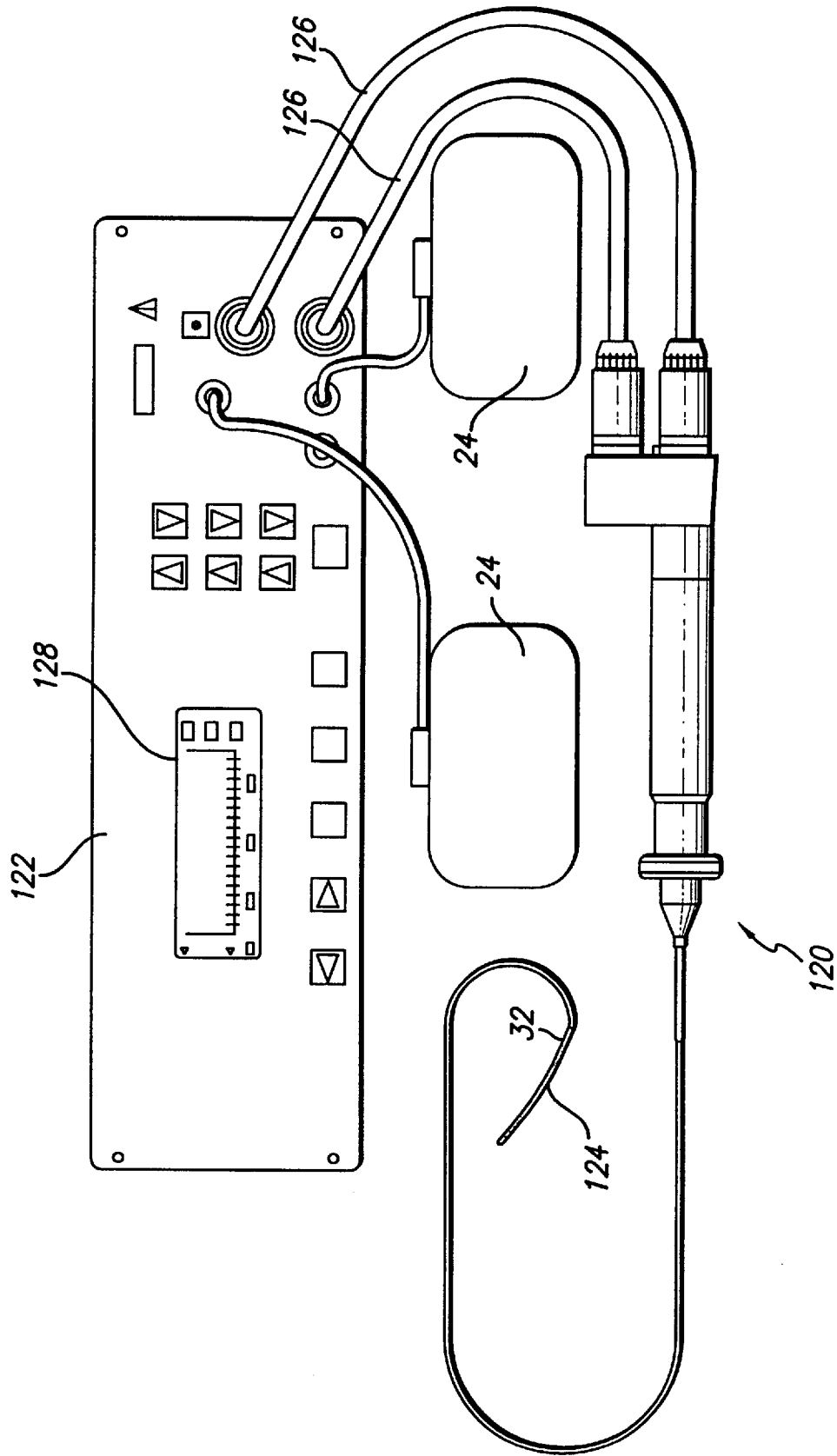

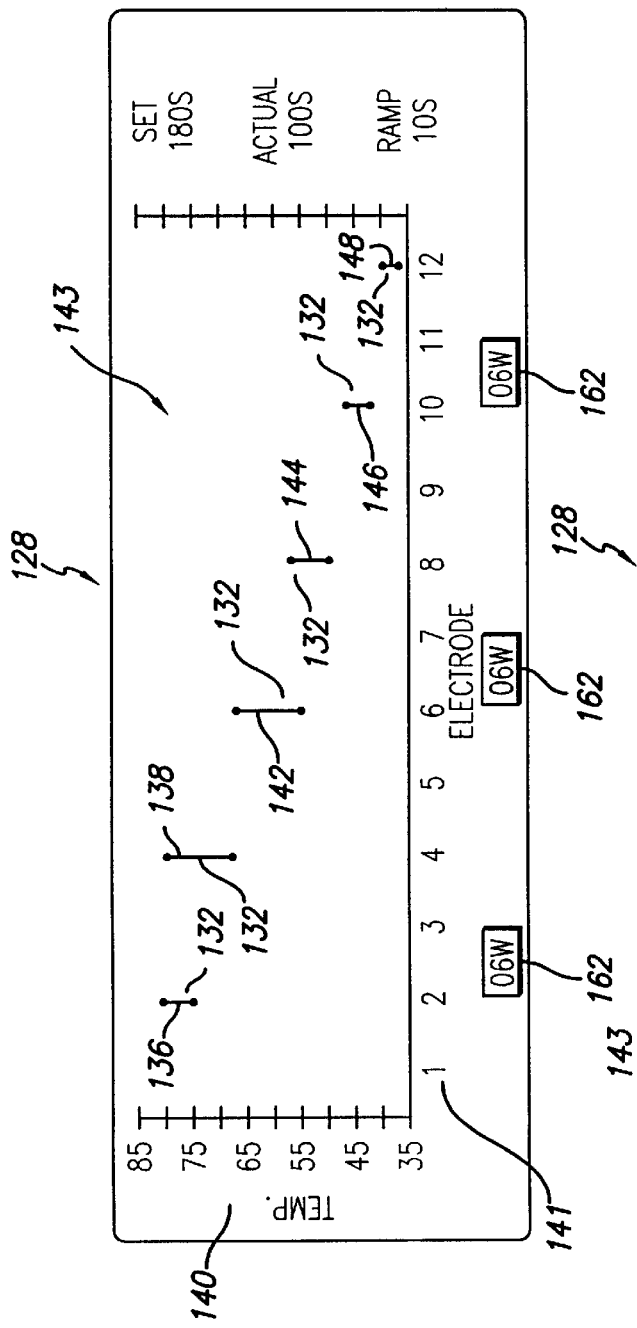
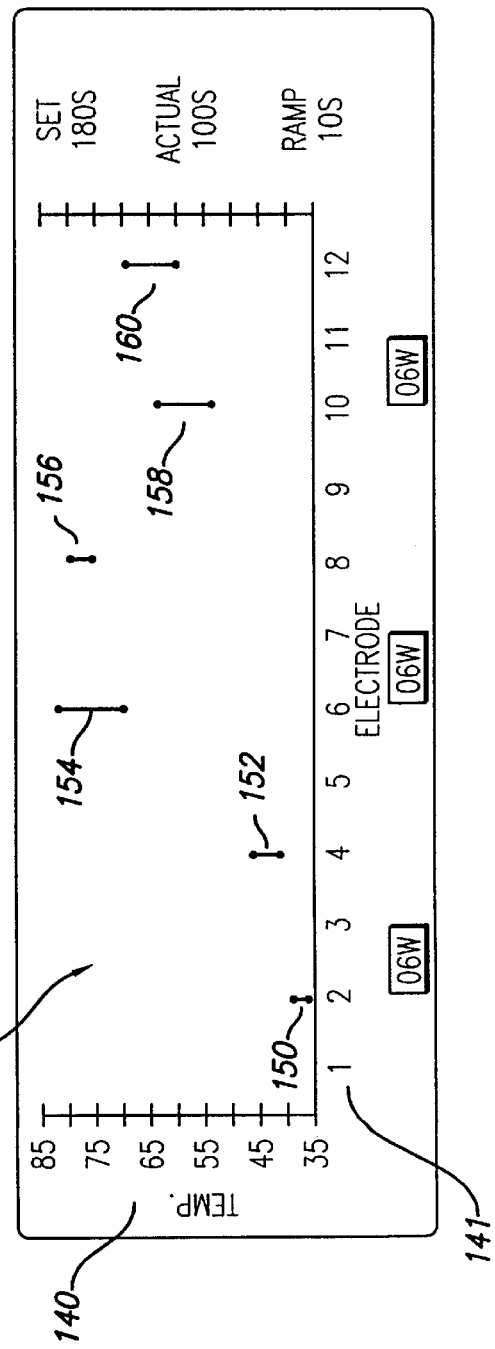

ABLATION SYSTEM AND METHOD HAVING MULTIPLE-SENSOR ELECTRODES TO ASSIST IN ASSESSMENT OF ELECTRODE AND SENSOR POSITION AND ADJUSTMENT OF ENERGY LEVELS

BACKGROUND OF THE INVENTION

The invention relates generally to an electrophysiological ("EP") apparatus and method for providing energy to biological tissue, and more particularly, to an ablation system having multiple-sensor electrodes and a controller for assessing the position of the electrode and the sensors relative to the biological tissue and the adequacy of the energy being applied.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In the bipolar method, the flux traveling between the two electrodes of the catheter enters the tissue to cause ablation.

During ablation, the electrodes are placed in intimate contact with the target endocardial tissue. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C.

During ablation, portions of the electrodes are typically in contact with the blood, so that it is possible for clotting and boiling of blood to occur if those electrodes reach an excessive temperature. Both of these conditions are undesirable. Clotting is particularly troublesome at the surface of the catheter electrode because the impedance at the electrode rises to a level where the power delivery is insufficient to effect ablation. The catheter must be removed and cleaned before the procedure can continue. Additionally, too great a rise in impedance can result in tissue dessication and thrombus formation within the heart, both of which are also undesirable. Further, too great a temperature at the interface between the electrode and the tissue can cause the tissue to reach a high impedance which will attenuate and even block the further transmission of RF energy into the tissue thereby interfering with ablation of tissue at that location.

To avoid these detrimental conditions, RF ablation catheters for cardiac applications typically provide temperature feedback during ablation via a thermal sensor such as a thermocouple. In the case where a catheter has a band electrode, such as for the treatment of atrial fibrillation by the ablation of tissue, the temperature reading provided by a single thermal sensor mounted to the band along the catheter's outside radius of curvature, may not accurately represent the temperature of the electrode/tissue interface. Typically the side of the band which is in direct contact with the tissue becomes significantly hotter than the rest of the band electrode that is cooled by the blood flow. Thus, the closer the thermal sensor is to the electrode/tissue interface, the more closely the temperature reading provided by the thermal sensor reflects the temperature of the tissue.

The position of the thermal sensor relative to the electrode/tissue interface is influenced by the rotational orientation of the catheter. If the catheter is oriented so that the single thermal sensor is not in contact with the tissue during the application of ablation energy, not only would there be a time lag in the sensor reaching the tissue temperature, but due to the effect of the cooling blood flow, the sensor reading may never approach the actual tissue temperature.

To overcome the effect that the rotational orientation of the catheter has on temperature sensing, two thermal sensors may be used. These thermal sensors are positioned at different locations on the band electrode and are also located about the catheter's outside radius of curvature, with one electrode being positioned on each side of the radius of curvature. As shown in FIGS. 15 and 16, the outside radius of curvature is the longitudinal line positioned at the outer most point of the outer half of the catheter, most distant from a reference center point of the catheter distal tip curve. Ideally, contact between the catheter and the tissue occurs along this longitudinal line, i.e., the outside radius of curvature. In such catheters it is generally assumed that at least one of the two thermal sensors will be located directly upon the electrode/tissue interface during ablation. Accordingly, while both thermal sensors provide temperature readings, only the highest measured temperature is of clinical interest. This is because the highest sensor reading is expected to reliably represent the electrode/tissue interface temperature.

In a catheter having two thermal sensors, it is still possible that neither sensor is positioned at the electrode/tissue interface. This may occur in situations where the contour of the anatomical structure in which the catheter is placed is such that the band electrode does not contact the tissue. This may also occur where the distal end of the catheter is misoriented such that while tissue contact is made, it is not made along the outside radius of curvature of the catheter. It may also occur where, due to excessive axial twisting of the distal end of the catheter, some of the band electrodes are rotated such that their thermal sensors are no longer oriented about the catheter's outside radius of curvature. In each of these situations it is possible that the temperature measurements provided by the thermal sensors may not accurately reflect the temperature of the electrode/tissue interface.

In order to provide sufficient electrical energy for effective ablation without unwittingly overheating the electrode/tissue interface and/or forming blood coagulum, it is necessary to first ensure that the electrodes contact the tissue, and second to ensure that the thermal sensors are positioned at or near the electrode/tissue interface so that reliable thermal monitoring of the ablation procedure may occur. For any given band electrode there are several possible scenarios for thermal sensor orientation relative to the electrode/tissue interface. In a first scenario, as shown in FIGS. 18a and 18b, one or both sensors is directly over the electrode/tissue interface. In a second scenario, as shown in FIGS. 19a and 19b, neither sensor is directly over the interface, but their orientation is adequate for one or both to still sense some heating. In a third scenario, as shown in FIGS. 20a and 20b, neither sensor is directly over the interface and their orientation is less than ideal to sense the tissue heating, or else the electrode is not making tissue contact at all (FIG. 20).

Based on the temperature measurement for the electrode it is possible to infer when the third scenario (FIGS. 20a and 20b) is being experienced by a particular band electrode during ablation because there is essentially no temperature response as the applied electrical energy is increased. Unfortunately, with a single temperature value one cannot readily distinguish between the first and second scenarios (FIGS. 18a, 18b and 19a, 19b, respectively) since either exhibits some temperature response with increasing ablation energy.

Hence, those skilled in the art have recognized a need for providing an RF ablation system having a catheter with an electrode carrying multiple thermal sensors for providing temperature readings at a plurality of locations on the electrode and for presenting those readings in a manner which assists in the assessment of both electrode position and thermal sensor position relative to the ablation tissue. The need for automatic control of the energy level applied to an electrode, in view of the electrode and thermal sensor position assessment, has also been recognized. The invention fulfills these needs and others.

SUMMARY OF THE INVENTION

Briefly, and in general terms, the invention is directed to an RF ablation system having multiple-sensor electrodes, which in combination with a controller, provide for the assessment of electrode position and thermal sensor position relative to the ablation tissue and assessment/adjustment of energy level application in view of the electrode and thermal sensor positions.

In one aspect, the invention relates to an apparatus for determining the position of a plurality of thermal sensors relative to biological tissue undergoing the application of energy. The apparatus includes a device for commonly carrying the thermal sensors; a catheter for carrying the device and positioning the device proximal the biological tissue; and a processor responsive to the thermal sensors for determining the temperature of each thermal sensor. The apparatus also includes a display responsive to the processor for providing a graphic representation of the temperature of each thermal sensor relative to the temperature of each of the other thermal sensors wherein the graphic representation is indicative of the proximity of the thermal sensors to the biological tissue.

By providing a graphic representation of the temperature of each thermal sensor relative to the temperature of each of the other thermal sensors that is indicative of the proximity of the thermal sensors to the biological tissue, the user is provided with additional information that may aid in deciding whether to adjust the position or orientation of the device relative to the tissue and whether to adjust the applied electrical energy to the catheter's device during the application of therapy.

In a more detailed aspect, the graphic representation is a bar graph with the temperature of each of the thermal sensors contained within the bar graph. By displaying each of the temperatures in a bar graph, the present invention facilitates rapid visual assimilation of current device/thermal sensor position and orientation. In another aspect, there are two thermal sensors and the graphic representation is a bar graph having the temperature of the first thermal sensor at a first end of the bar graph and the temperature of the second thermal sensor at a second end of the bar graph. In a further facet, the display includes a temperature-range region for displaying an upper temperature range generally indicative of direct contact between at least one of the thermal sensors and the tissue, a middle temperature range generally indicative of near contact between at least one of the thermal sensors and the tissue and a lower temperature range generally indicative of no contact between the thermal sensors and the tissue. The display further includes a device region for displaying a device indicator for each of the devices; and a temperature-data region for displaying a graphic representation which correlates the temperature-range region and the device region to indicate the temperature of the thermal sensors associated with a particular device.

In another facet, the invention is an apparatus for applying energy to biological tissue. The apparatus includes a plurality of electrodes, each with at least one thermal sensor. The apparatus further includes a catheter for carrying the electrodes and positioning the electrodes proximal the biological tissue; a processor responsive to each of the thermal sensors for determining the temperature of the thermal-sensor/electrode junction; and a display responsive to the processor for providing a graphic representation of the temperature of each of the thermal-sensor/electrode junctions relative to the temperature of each of the other thermal-sensor/electrode junctions wherein such representation is indicative of the proximity of each thermal-sensor/electrode junction to the biological tissue.

In a more detailed facet, the plurality of electrodes have at least two thermal sensors and the graphic representation is a bar graph having the temperature of the first thermal sensor at a first end of the bar graph and the temperature of the second thermal sensor at a second end of the bar graph. In another aspect, the length of the bar graph combined with the position of the bar graph relative to the temperature-range region provides an indication of the position of the thermal-sensor/electrode junctions relative to the biological tissue.

In another aspect, the invention is related to an ablation procedure using a catheter having at least one electrode carrying a plurality of thermal sensors and involves a method for determining the position of the thermal sensors relative to the biological tissue undergoing ablation. The method includes monitoring the temperature of each thermal sensor; specifying an upper temperature range generally indicative of direct contact between at least one of the thermal sensors and the tissue; specifying a middle temperature range generally indicative of near contact between at least one of the thermal sensors and the tissue; specifying a lower temperature range generally indicative of no contact between the thermal sensors and the tissue and comparing the monitored temperatures to the temperature ranges.

In a detailed facet, the method also includes, if at least one of the temperatures is within the upper temperature range, maintaining the present position of the electrode relative to the tissue. In another aspect, the method also includes, if each of the temperatures is within the middle temperature range, maintaining the present position of the electrode relative to the tissue. In yet another aspect, the method includes, if each of the temperatures is within the lower temperature range, repositioning the electrode relative to the tissue such that the temperatures are within either one of the middle temperature range or the middle temperature range. In still another facet, comparing the monitored temperatures includes: for each electrode, providing a graphic representation of the temperature of the thermal sensors; and comparing the graphic representation to the upper, middle and lower temperature ranges.

In another facet, the invention is related to an ablation procedure using a catheter having at least one electrode carrying a plurality of thermal sensors, and involves a method of monitoring the application of energy to the biological tissue undergoing ablation. The method includes: (a) positioning the electrode proximal the biological tissue to be ablated; (b) applying a constant energy level to the electrode for a specified period of time; (c) at the end of the specified period of time, determining the temperature of each thermal sensor; (d) displaying the temperature of each thermal sensor; (e) if necessary, adjusting the level of energy applied to the electrode; and (f) if necessary, adjusting the orientation of the electrode relative to the tissue.

In a detailed facet, adjusting the energy level applied to the electrode includes: specifying an upper temperature range generally indicative of direct contact between at least one of the thermal sensors and the tissue; specifying a middle temperature range generally indicative of near contact between the thermal sensors and the tissue; and specifying a lower temperature range generally indicative of no contact between the thermal sensors and the tissue. Adjusting the energy level applied to the electrode further includes: comparing the temperatures of each thermal sensor to the lower, middle and lower temperature ranges; if each of the temperatures is within the upper temperature range, adjusting the energy level such that the temperatures of the thermal sensors are substantially maintained at the temperature necessary to cause ablation; and if each of the temperatures is within the middle temperature range, maintaining the energy level at its present value such that the temperatures of the thermal sensors are maintained within the middle temperature range. In another detailed aspect, adjusting the orientation of the electrodes includes: specifying an upper temperature range generally indicative of direct contact between the thermal sensors and the tissue; specifying a middle temperature range generally indicative of near contact between the thermal sensors and the tissue; specifying a lower temperature range generally indicative of no contact between the thermal sensors and the tissue; comparing the temperatures of each thermal sensor to the upper, middle and lower temperature ranges; and if each of the temperatures is within the lower temperature range, repositioning the electrode relative to the tissue and repeating steps (b) through (f).

In still another aspect, the invention relates to a method of, and an apparatus for, controlling the application of energy to the biological tissue during an ablation procedure using an electrode having at least two thermal sensors attached at separate points. The thermal sensors provide temperature signals indicative of the temperatures of the electrode at the attachment points. The method includes applying power to the electrode while monitoring the spread between the temperatures of the at least two thermal sensors and if the spread exceeds a threshold value, reducing the power. The apparatus includes a generator for applying power to the electrode and a processor programmed to store a threshold value, monitor the spread between the temperatures of the at least two thermal sensors, and cause the generator to reduce the power applied by the generator when the spread exceeds the threshold value.

In yet another aspect, the invention relates to a method of, and an apparatus for, controlling the application of energy to the biological tissue during an ablation procedure. The procedure is done using a catheter comprising a plurality of electrodes. At least two of the electrodes are multiple-sensor electrodes having at least two thermal sensors attached at separate points for providing temperature signals indicative of the temperatures of the electrode at the points of attachment. The method includes, for each multiple-sensor electrode, applying power to the multiple-sensor electrode while monitoring the spread between the temperatures of the at least two thermal sensors associated with the multiple-sensor electrode and if any one of the spreads exceeds a threshold value, at least reducing the power to the multiple-sensor electrode associated with that spread. The apparatus includes a generator operating under the control of a processor to apply power to each multiple-sensor electrode. The processor is programmed to, for each multiple-sensor electrode, monitor the spread between the temperatures of the at least two thermal sensors associated with the multiple-sensor electrode and if any one of the spreads exceeds a threshold value, cause the generator to reduce the power to at least the multiple-sensor electrode associated with that spread.

In another facet, the invention relates to an apparatus for controlling the application of energy to the biological tissue during a tissue ablation procedure using a catheter comprising a plurality of electrodes. At least two of the electrodes have multiple-sensor electrodes having two thermal sensors attached at separate points for providing temperature signals indicative of the temperatures of the electrode at the points of attachment. The apparatus includes a generator operating under the control of a processor to apply power to each multiple-sensor electrode. The processor is programmed to store a target temperature and a spread threshold; for each multiple-sensor electrode, monitor the temperatures of each sensor to first identify those electrodes having at least one temperature that is at least as great as the target temperature for each first identified electrode, monitor the spread between the temperature of the two thermal sensors to second identify those electrodes having a spread less than the spread threshold; compare the power levels of each of the second identified electrodes to third identify the electrode having the lowest power level; and cause the generator to set the power level to each of the multiple-sensor electrodes to a power level substantially equal to the power level of the third identified electrode.

These and other aspects and advantages of the invention will become apparent from the following detailed description and the accompanying drawings, which illustrate by way of example the features of the invention.

BRIEF DESCRIPTION OF THE DRAWINGS

FIG. 4 depicts a first power waveform having a first phase angle and alternating instances of peak power and very low power;

FIG. 5 depicts a second power waveform having a second phase angle different from the first phase angle and alternating instances of peak power and very low power;

FIG. 6 presents a time frame (TF) diagram showing a fifty-percent duty cycle;

FIGS. 8A, 8B, 8C, 8D, and 8E are schematic diagrams of an embodiment of a power control system in accordance with aspects of the invention with FIG. 8A showing how FIGS. 8B, 8C, 8D and 8E are related;

FIG. 14 depicts an RF ablation system including a catheter, backplates and an RF generator/controller;

FIG. 17 is the display portion of the RF generator/controller front panel of FIG. 14, depicting, in bar-graph format, the relative temperatures of several of the distal-region band electrodes;

FIG. 21 depicts in bar-graph format, the relative temperatures of several of the distal-region band electrodes.

DETAILED DESCRIPTION OF PREFERRED EMBODIMENTS

Figure 1:
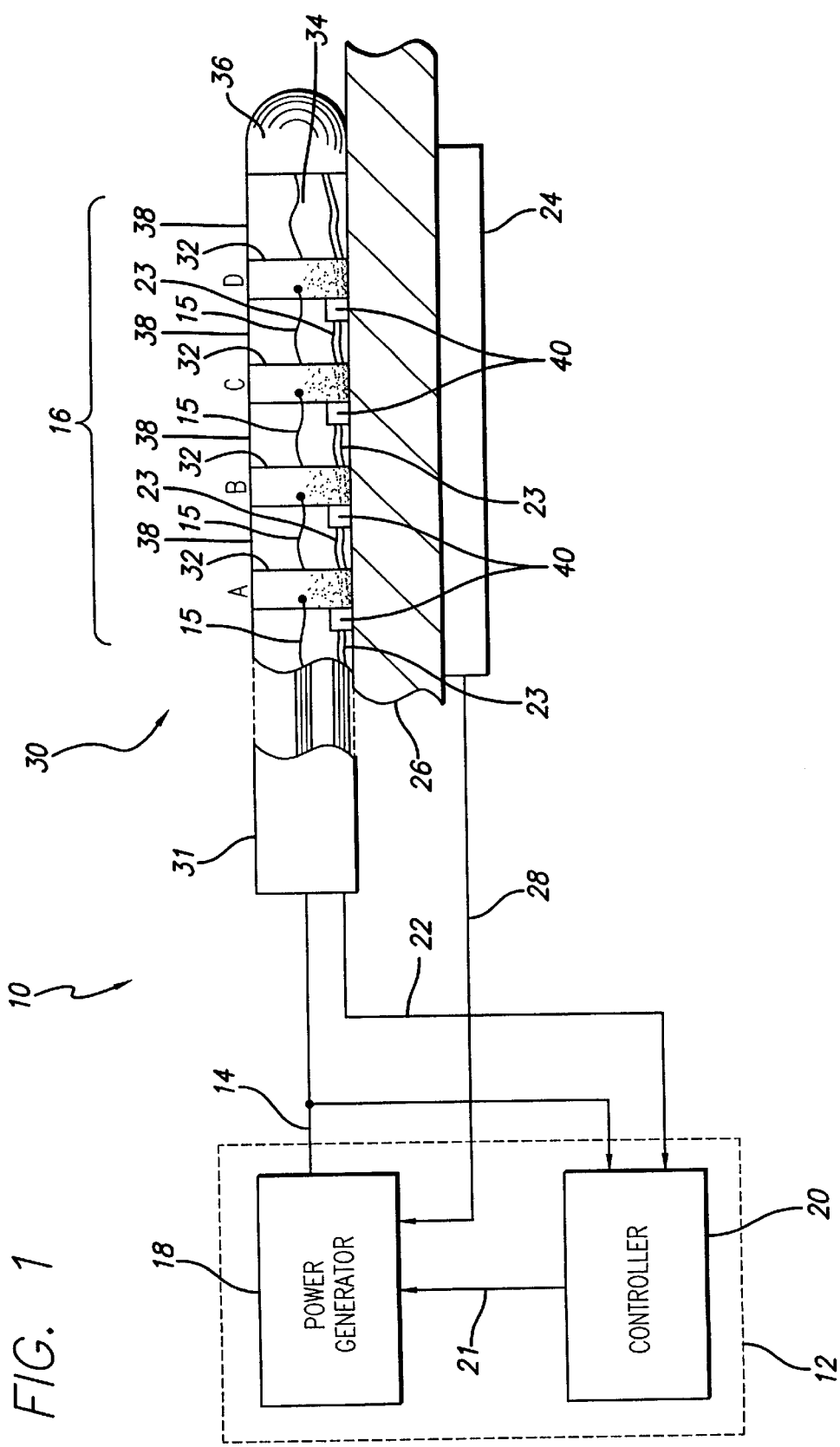
FIG. 1 is a schematic diagram of an ablation apparatus including a power control system, electrode device and backplate.

Turning now to the drawings, in which like reference numerals are used to designate like or corresponding elements among the several figures, in FIG. 1 there is shown an ablation apparatus 10 in accordance with aspects of the present invention. The apparatus 10 includes a power control system 12 that provides power or drive 14 to an electrode device 16. The power control system 12 comprises a power generator 18 that may have any number of output channels through which it provides the power 14. The operation of the power generator 18 is controlled by a controller 20 or processor which outputs control signals 21 to the power generator 18. The controller 20 monitors the power 14 provided by the power generator 18. In addition, the controller 20 also receives temperature signals 22 from the electrode device 16. Based on the power 14 and temperature signals 22 the controller 20 adjusts the operation of the power generator 18. A backplate 24 is located proximal to the biological site 26 opposite the site from the electrode device 16, and is connected by a backplate wire 28 to the power generator 18. The backplate 24 is set at the reference level to the power provided to the electrodes, as discussed in detail below.

The electrode device 16 is typically part of a steerable EP catheter 30 capable of being percutaneously introduced into a biological site 26, e.g., the atrium or ventricle of the heart. The electrode device 16 is shown in schematic form with the components drawn to more clearly illustrate the relationship between the components and the relationship between the components and the power control system 12. In this embodiment, the catheter 30 comprises a distal segment 34 and a handle 31 located outside the patient. A preferred embodiment of the electrode device 16 includes twelve band electrodes 32 arranged in a substantially linear array along the distal segment 34 of the catheter 30. The electrode device 16 may include a tip electrode 36. (For clarity of illustration, only four band electrodes 32 are shown in the figures although as stated, a preferred embodiment may include many more.) The band electrodes 32 are arranged so that there is space 38 between adjacent electrodes. In one configuration of the electrode device 16, the width of the band electrodes 32 is 3 mm and the space 38 between the electrodes is 4 mm. The total length of the electrode device 16, as such, is approximately 8 cm.

The arrangement of the band electrodes 32 is not limited to a linear array and may take the form of other patterns. A substantially linear array is preferred for certain therapeutic procedures, such as treatment of atrial fibrillation, in which linear lesions of typically 4 to 8 cm in length are desired. A linear array is more easily carried by the catheter 30 and also lessens the size of the catheter.

The band electrodes 32 are formed of a material having a significantly higher thermal conductivity than that of the biological tissue 26. Possible materials include silver, gold, chromium, aluminum, molybdenum, tungsten, nickel, platinum, and platinum/10% iridium. Because of the difference in thermal conductivity between the electrodes 32 and the tissue 26, the electrodes 32 cool off more rapidly in the flowing fluids at the biological site. The power supplied to the electrodes 32 may be adjusted during ablation to allow for the cooling of the electrodes while at the same time allowing for the temperature of the tissue to build up so that ablation results. The electrodes 32 are sized so that the surface area available for contact with fluid in the heart, e.g., blood, is sufficient to allow for efficient heat dissipation from the electrodes to the surrounding blood. In a preferred embodiment, the electrodes 32 are 7 French (2.3 mm in diameter) with a length of 3 mm.

Associated with the electrode device 16 are thermal sensors 40 for monitoring the temperature of the electrode device 16 at various points along its length. In one embodiment, each band electrode 32 has a thermal sensor 40 mounted to it. Each thermal sensor 40 provides a temperature signal 22 to the controller 20 which is indicative of the temperature of the respective band electrode 32 at that sensor. In another embodiment of the electrode device 16 a thermal sensor 40 is mounted on every other band electrode 32. Thus for a catheter having twelve electrodes, there are thermal sensors on six electrodes. In yet another embodiment of the electrode device 16 every other electrode has two thermal sensors 40. In FIG. 1, which shows an embodiment having one thermal sensor for each electrode, there is shown a single power lead 15 for each electrode 32 to provide power to each electrode for ablation purposes and two temperature leads 23 for each thermal sensor 40 to establish the thermocouple effect.

In another approach, the power lead may comprise one of the thermocouple wires or may comprise a common wire for a plurality of thermocouples mounted on the same electrode. The inventors hereby incorporate by reference U.S. Pat. No. 6,049,737 entitled "Catheter Having Common Lead for Electrode and Sensor", U.S. Pat. No. 6,045,550 entitled "Electrode Having Non-Joined Thermocouple for Providing Multiple Temperature-Sensitive Junctions" and U.S. Pat. No. 6,042,580 entitled "Electrode Having Composition-Matched, Common-Lead Thermocouple Wire For Providing Multiple Temperature-Sensitive Junctions".

Figures 1, 2:
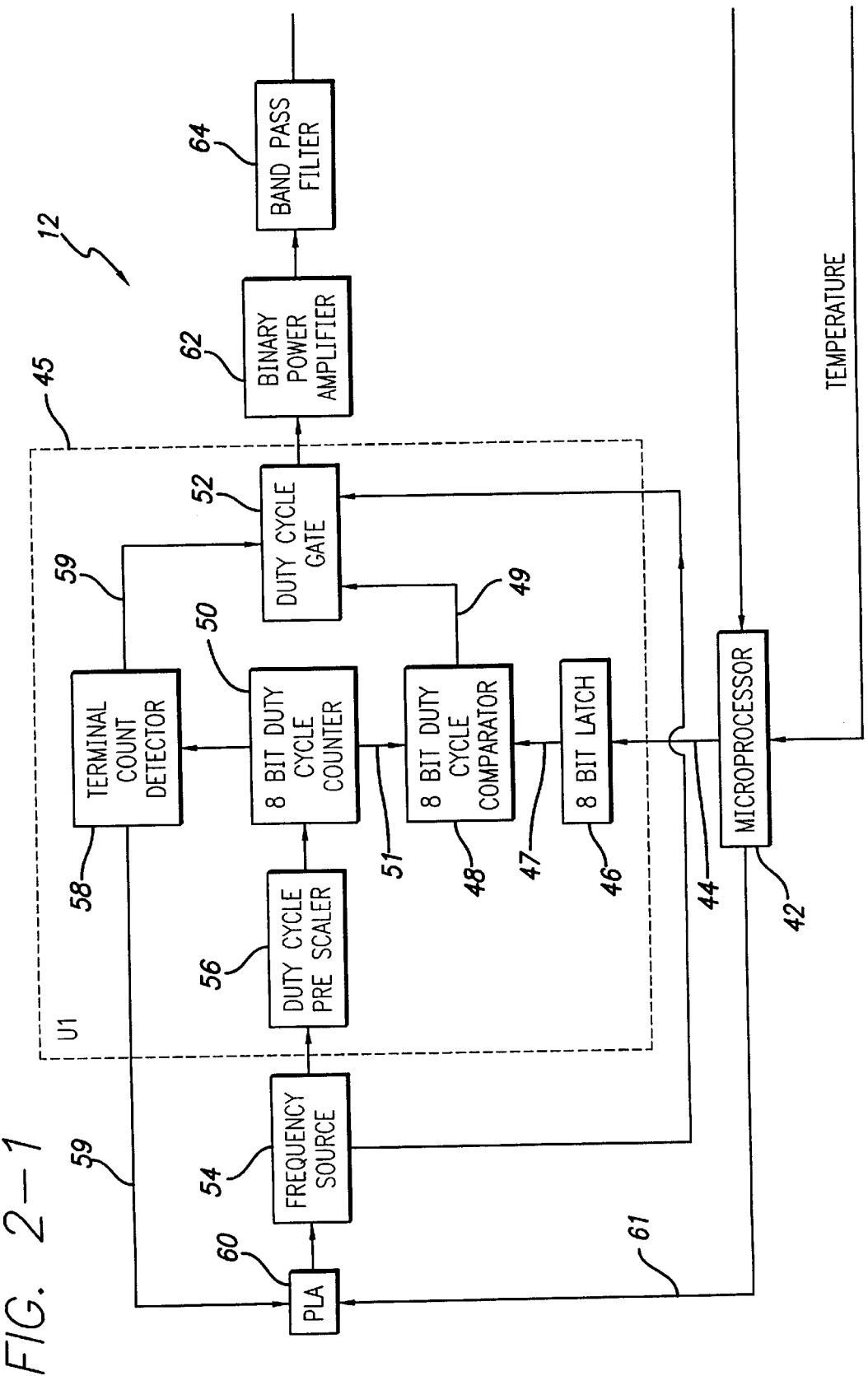
FIG. 2 is a block diagram presenting more detail of a power control system in accordance with aspects of the invention, showing phase angle control, duty cycle control, and impedance and temperature monitoring.
Figure 2:
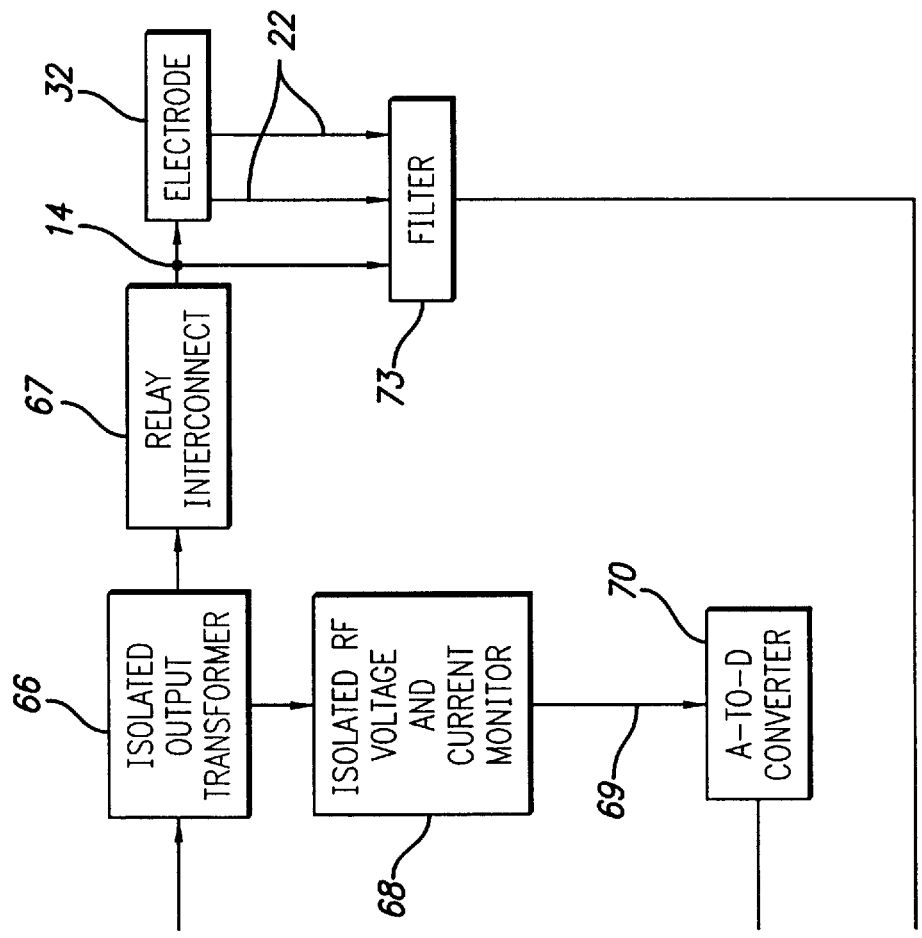

Turning now to FIGS. 2-1 and 2-2, a block diagram of an ablation apparatus 10 and method in accordance with aspects of the invention is presented. In FIGS. 2-1 and 2-2, a single channel of the power control system 12 is depicted. This channel controls the application of power to a single electrode 32. As will be discussed in relation to other figures, a channel may control a plurality or group of electrodes. In FIG. 2-1, a microprocessor 42, which is part of the controller 20 (FIG. 1), provides a duty cycle control signal 44 to a duty cycle generator 45. In this case, the duty cycle generator 45 receives the control signal 44 by an 8-bit latch 46. The latch 46 provides an 8-bit signal 47 to a duty cycle comparator ("DCG") 48. The comparator 48 compares the 8-bit signal 47 to a count from an 8-bit duty cycle counter 50 and if the count is the same, provides a duty cycle off signal 49 to the duty cycle gate 52. The gate 52 is connected to a frequency source ("FS") 54, such as an oscillator that produces 500 kHz. When the gate 52 receives the duty cycle off signal 49 from the comparator 48, it stops its output of the frequency source signal through the gate and no output exists.

At a frequency of 500 kHz, an 8-bit control has a period or time frame of 0.5 msec. At a fifty-percent duty cycle, the electrode is in the off period only 0.25 msec. To allow for greater cooling of the electrode, the period or time frame 78 (FIG. 6) is lengthened by use of a prescalar 56 interposed between the frequency source 54 and the counter 50. In one embodiment, the prescalar 56 lengthens the period to 4 msec thus allowing for a 2 msec off period during a fifty-percent duty cycle. This results in a sufficient cooling time for the very thin band electrodes discussed above. Other lengths of the period may be used depending on the circumstances. It has been found that a ten percent duty cycle is particularly effective in ablating heart tissue. The combination of the application of high peak power, a ten percent duty cycle, the use of high thermal conductivity material in the band electrodes, and fluids flowing past the band electrodes which have a cooling effect on the electrodes result in a much more effective application of power to the tissue. Ablation occurs much more rapidly.

A terminal count detector 58 detects the last count of the period and sends a terminal count signal 59 to the gate 52 which resets the gate for continued output of the frequency source signal. This then begins the on period of the duty cycle and the counter 50 begins its count again. In one preferred embodiment, the duty cycle is set at fifty percent and the 8-bit latch is accordingly set to 128. In another embodiment, the duty cycle is set at ten percent.

A programmable logic array ("PLA") 60 receives phase control signals 61 from the microprocessor 42 and controls the phase of the frequency source 54 accordingly. In one embodiment, the PLA 60 receives the terminal count signal 59 from the terminal count detector 58 and only permits phase changes after receiving that terminal count signal.

The output signal from the gate 52 during the on period of the duty cycle is provided to a binary power amplifier ("BPA") 62 that increases the signal to a higher level, in this case, 24 volts. The amplified signals are then filtered with a band pass filter ("BPF") 64 to convert the somewhat square wave to a sine wave. The band pass filter 64 in one embodiment is centered at 500 kHz. The filtered signal is then provided to an isolated output transformer ("IOT") 66 that amplifies the signal to a much higher level, for example 350 volts peak-to-peak. This signal is then sent to a relay interconnect ("RI") 67 before it is provided as a power output signal OUTn 14 to an electrode 32 at the biological site to cause ablation.

The power output signal 14 from the isolated output transformer 66 is monitored in one embodiment to determine the impedance at the electrode 32. In the embodiment shown in FIGS. 2-1 and 2-2, a voltage and current monitor ("VCM") 68 is used. The monitor signal 69 is converted to digital form by an A-to-D converter ("ADG") 70 and provided to the microprocessor 42. As previously mentioned, some or all of the electrodes 32 may include a thermal sensor 40 (FIG. 1) that provides temperature signals 22 (FIG. 2-2) which are used to determine the temperature at the electrode 32. In one embodiment of the invention, the power 14, in conjunction with the temperature signals 22, are used to determine the temperature at the electrode 32. Both the temperature signals 22 and the power 14 pass through a temperature filter 73 before being sent to the microprocessor 42. In the alternative, the temperature filter ("FL") 73 is contained in a printed circuit board separate from the controller 20 and contains its own processor. In either case, the filter 73 filters out any RF noise present in the power 14 so that the signal may be used for temperature monitoring purposes. In another embodiment, the microprocessor monitors the power 14 and temperature signals 22 only during the off periods of the power 14 duty cycle. Accordingly, negligible RF noise is present in the power line and filtration is not necessary. In either embodiment, the microprocessor 42 may alter the duty cycle of the power 14 in response to either or both of the impedance or temperature signals.

Figure 3:
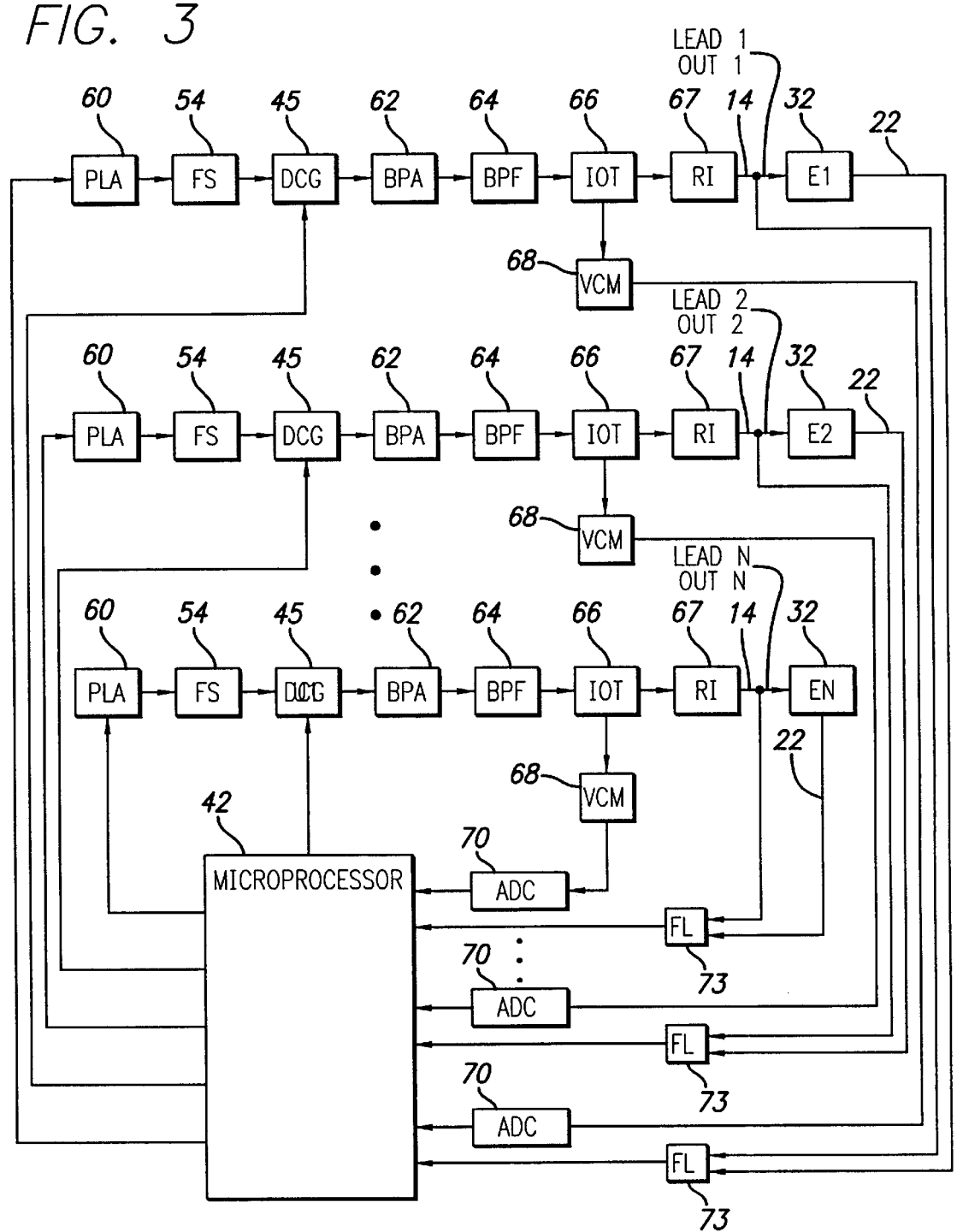
FIG. 3 is a diagram of a multi-channel ablation apparatus in accordance with aspects of the invention wherein a single microprocessor controls the phase angle and duty cycle of each channel individually.

Referring now to FIG. 3, a multiple channel ablation apparatus is shown. Although only three complete channels are shown, the apparatus comprises many more as indicated by the successive dots. Those channels are not shown in FIG. 3 to preserve clarity of illustration. By providing different voltage levels between two electrodes 32 in an array, current flows between those electrodes in a bipolar electrode approach. By setting the backplate 24 (FIG. 1) at a voltage level different from at least one of those electrodes 32, current flows between that electrode and the backplate. By controlling the voltage levels among the three (two electrodes and backplate), the current flow through the biological site 26 can be more precisely controlled. One technique for setting different voltage levels between the electrodes 32 is to maintain a phase difference between them in an AC approach. By setting the backplate 24 at the reference level, current flows between the electrodes 32 and the backplate.

The single microprocessor 42, which again is part of the controller 20 (FIG. 1), controls the duty cycle and the phase of each channel individually in this embodiment. Each channel shown comprises the same elements and each channel produces its own power output signal 14 (OUT1, OUT2, through OUTn where "n" is the total number of channels) on respective electrode leads (LEAD 1, LEAD 2, through LEAD n where "n" is the total number of leads) to the electrodes 32. This multi-channel approach permits more individual control over each electrode. For example, the duty cycle of the power applied to each electrode can be individually controlled. One electrode may have a ten percent duty cycle while another has a thirty percent duty cycle.

Referring now to the first and second output signals OUT1 and OUT2 of FIG. 3, the signals, as shown in FIGS. 4, 5, and 6, have alternating instances of peak power i.e., "on" periods 74, and very low power 76, i.e., "off" periods. Typically, the output power 14 is a 500 kHz sine wave. In FIGS. 4 and 5, the number of cycles of the sine wave contained within one on period 74 has been substantially reduced in the drawing to emphasize the phase difference between the first and second output signals OUT1, OUT2. Preferably, the voltage of each power signal 14 during an off period 76 is substantially zero and during an on period 74 is approximately 350 volts peak-to-peak.

The power OUT1 and OUT2 also have a variable duty cycle for controlling the length of the on period 74 and the off-period 76 within a time frame 78 (see FIG. 6). The duty cycle is the ratio of the length of the on period 74 to the length of the entire time frame 78. The effective power is the peak power times the duty cycle. Thus, a signal having a peak power of 100 watts and a 50% duty cycle has an effective power of 50 watts.

Figure 7B:
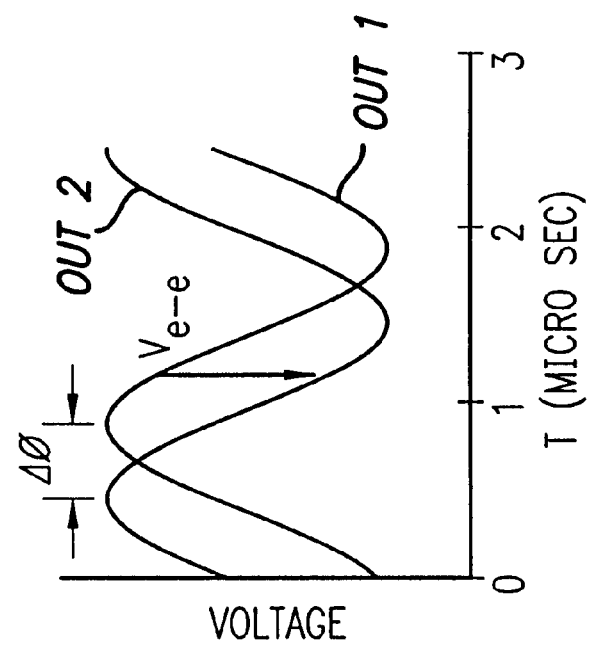
FIG. 7B depicts the phase relationship and voltage potential between the first and second power waveforms having second and first phase angles respectively, as a function of time.
Figure 7A:
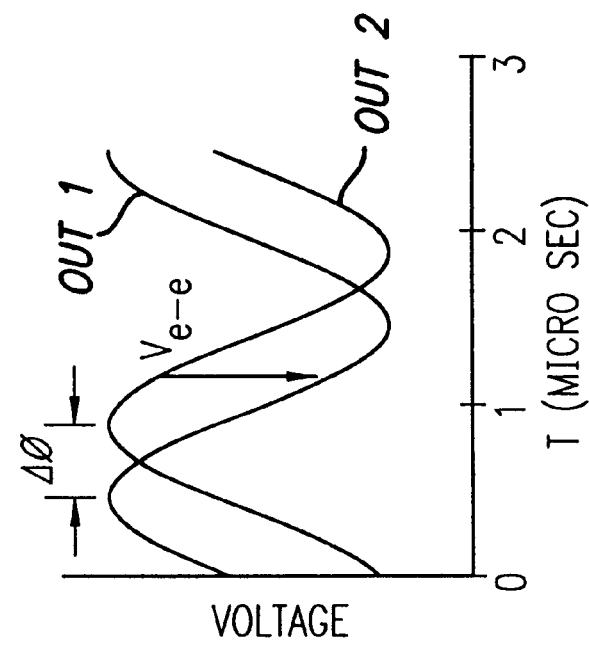
FIG. 7A depicts the phase relationship and voltage potential between the first and second power waveforms having first and second phase angles respectively, as a function of time.

As shown in FIGS. 4, 5, and 6, the two power signals OUT1, OUT2 are phased differently from each other. As discussed above, the phase angle of each power signal is set and controlled by the processor 42 and PLA 60. Each power signal OUT1 and OUT2 has a respective phase angle and those phase angles differ between the two of them. The phase angle difference between the power OUT1 and OUT2 produces a voltage potential between the band electrodes 32 (FIG. 1) that receive the power. This voltage potential, in turn, induces current flow between the band electrodes 32. The phase angle relationship of the power and the voltage potential produced as a function of time is shown in FIGS. 7A and 7B. The potential between electrodes $V_{e-e}$ is defined by:

$$V_{e-e} = 2V\sin\left(\frac{\Delta\Phi}{2}\right)\sin(2\pi ft) \qquad \text{(Eq. 1)}$$

where:
$\Delta\Phi$=phase angle difference between electrodes
V=voltage amplitude of power
f=frequency in hertz
t=time FIG. 7A shows first and second power OUT1 and OUT2 provided to first and second electrodes respectively having a phase angle difference $\Delta\Phi$ with OUT1 leading OUT2 by 132 degrees. FIG. 7B shows the same power OUT1 and OUT2 but with the phase angles reversed where OUT2 is now leading OUT 1 by 132 degrees.

Figure 8C:
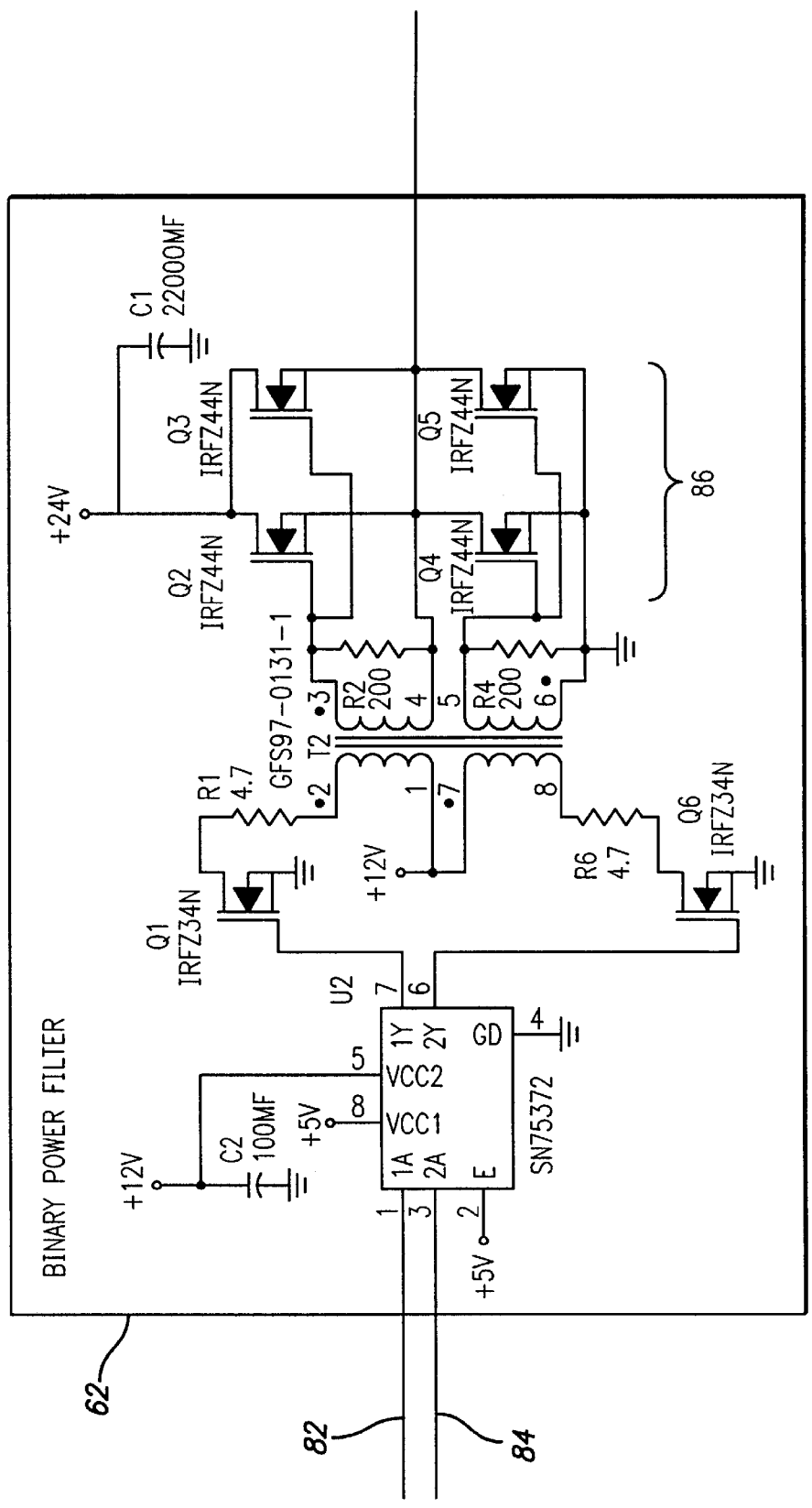
Figure 8D:
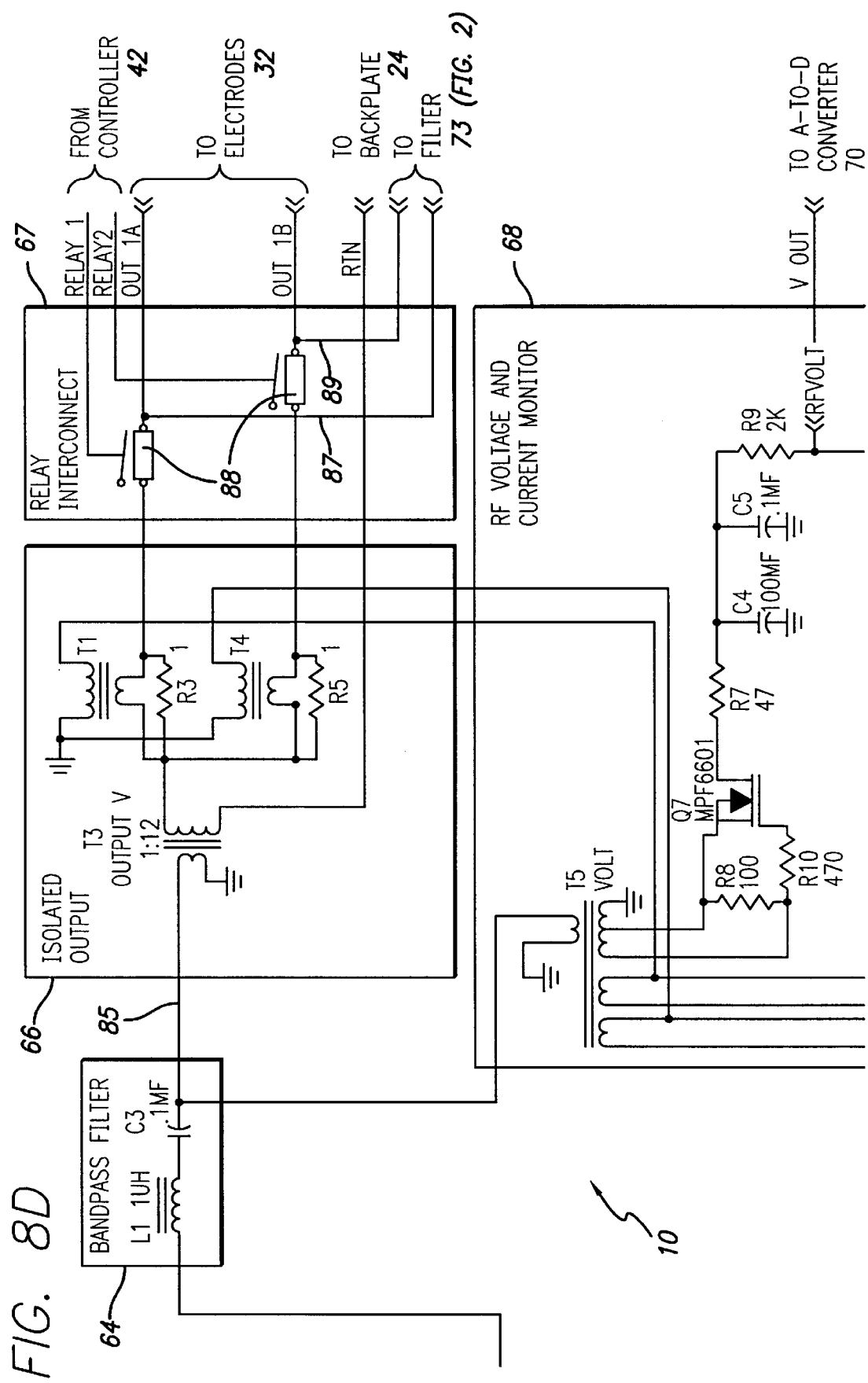
Figure 8E:
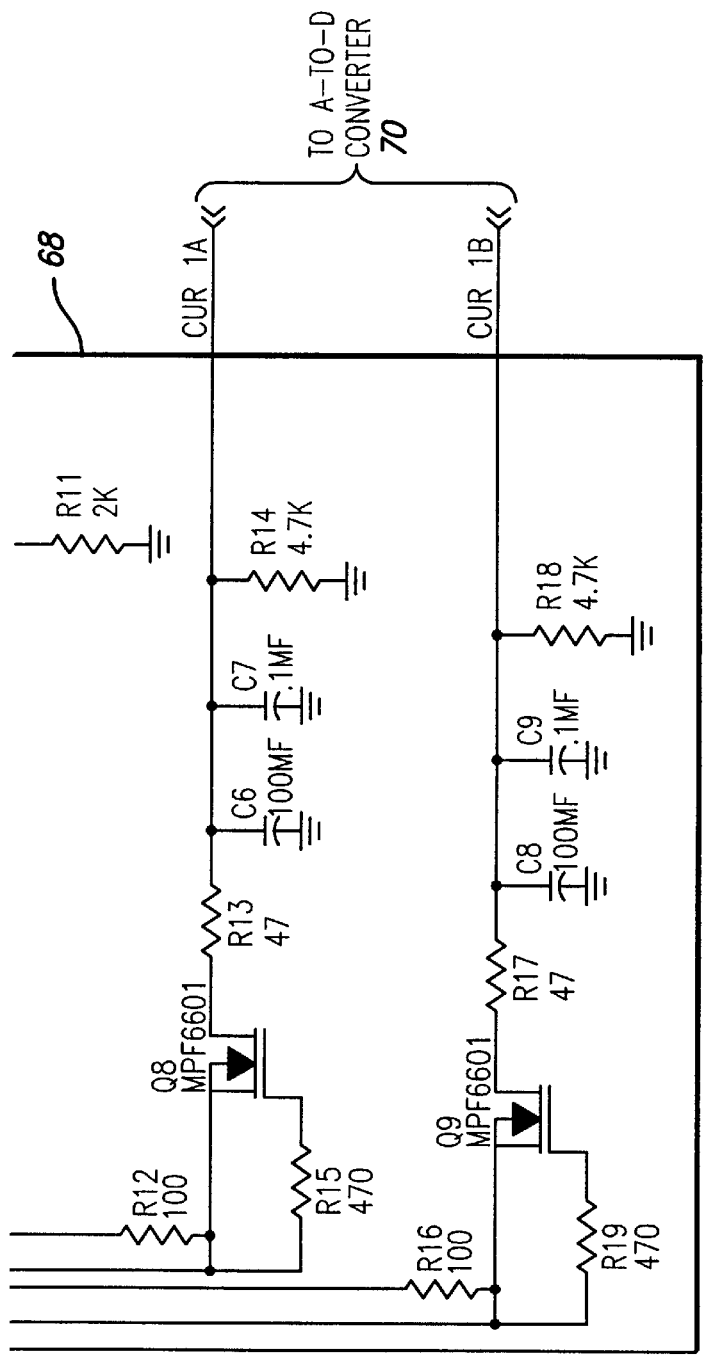
Figure 9A:
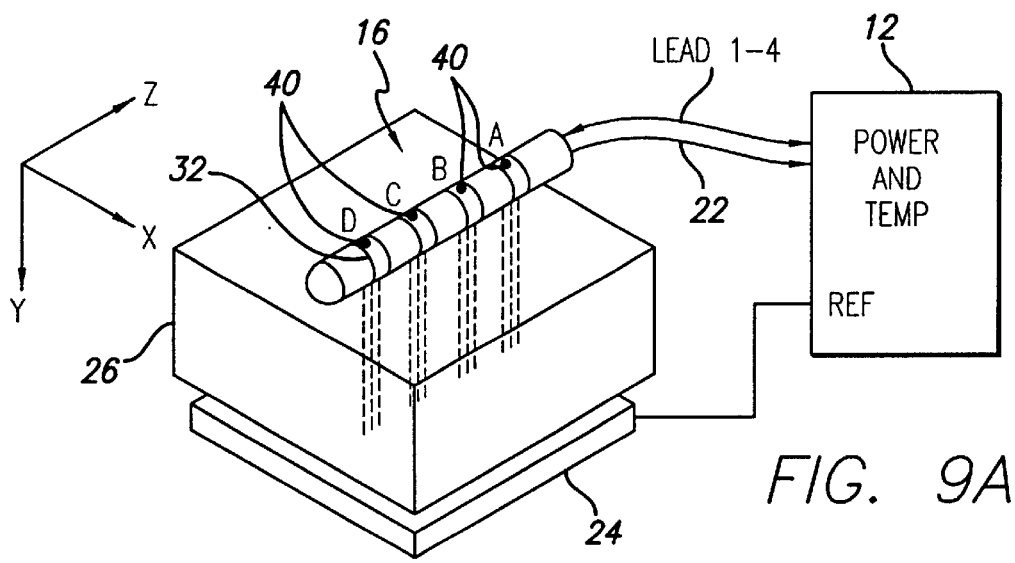
FIG. 9A is a three dimensional representation of an ablation apparatus having a linear array of band electrodes in contact with a biological site with a backplate at the opposite side of the biological site, in which the phase angle difference between adjacent electrodes of the linear array is zero degrees.
Figure 9B:
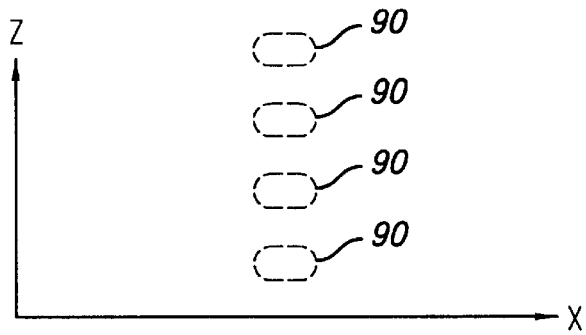
FIGS. 9B through 9D depict, along the x, y, and z axes shown, the depth of the lesions formed by the ablation apparatus of FIG. 9A showing that the apparatus acts as a unipolar device with multiple electrodes and the resulting lesions are discontinuous.
Figure 9C:
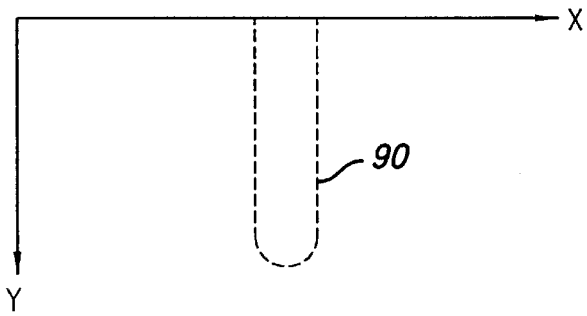
Figure 9D:
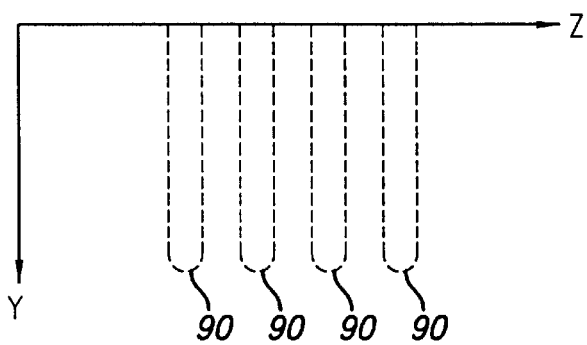

With reference now to FIGS. 8A through 8E, schematic diagrams of an embodiment of the ablation apparatus 10 of FIGS. 2-1 and 2-2 are presented in FIGS. 8B through 8E while FIG. 8A shows how FIGS. 8B through 8E should be oriented in relation to each other. The frequency source 54 provides a signal 80, typically at 500 kHz with a phase angle controlled by the microprocessor 42 through the PLA 60, to the duty cycle generator 45. The duty cycle generator 45 modulates the frequency source signal 80 to produce the selected duty cycle in accordance with the duty cycle control signal 44 as previously described. The duty cycle generator 45 outputs two signals 82 and 84 to the binary power amplifier 62. A dual MOSFET driver U2 receives the signals, converts their 5V level to a 12V level, and sends each to a transformer T2 which transforms the signals into 24 V peak-to-peak power.

The 24V power is then sent to a multi-state driver 86 which includes a configuration of FETs Q2, Q3, Q4, and Q5. During a conducting state of the driver 86, which is typically the on period 74 of the power, these FETs Q2 through Q5 conduct and forward the power to a bandpass filter 64 comprising a series LC network. During a high-impedance state of the driver 86, which is typically during the off period 76 of the power, the FETs Q2 through Q5 are non-conducting and no power is sent to the bandpass filter 64. Instead the FETs Q2 through Q5 present a high impedance load to any signals received through the electrode 32. Typically the load impedance on the FETs Q2 through Q5 presented by the circuit following the FETs, the electrode, and the tissue is approximately 150 Ω but transformed through the output transformer T3, it presents a load impedance to the FETs Q2–Q5 of approximately 0.5 to 1 Ω. In the off state, the FETs present an impedance of approximately 250 Ω which is large in comparison to the transformed load impedance of approximately 0.5 to 1 Ω. Therefore, very little power flows when the FETs are in the off state.

The bandpass filter 64 operates to shape the output signal provided by the binary amplifier 62 from a square wave to a sinusoidal wave. The filtered signal 85 then passes to the isolated output section 66 where it is step-up transformed to 350 volt peak-to-peak sinusoidal power at T3. The power is then split into two identical power signals OUT1A, OUT1B and provided to two or more respective band electrodes 32 on the output lines LEAD1A, LEAD1B.

The isolated output section 66 also includes relays 88 that may be individually opened to remove the power signals OUT1A, OUT1B from the electrode leads LEAD 1A, LEAD 1B when an alert condition is detected, such as high temperature or high impedance at the respective electrode 32. As previously mentioned these conditions are determined by the microprocessor 42 which receives signals indicative of the temperature and impedance at each of the band electrodes 32.

The power from the isolated output section 66 is monitored and representative signals are supplied to an RF voltage and current monitor 68 where in this case, the voltage and current of each output signal are measured to determine the impedance of the particular channel. The measured signals are sent to an A-to-D converter 70 (FIG. 2-2) before being sent to the microprocessor 42 for impedance monitoring. If the impedance is above a threshold level indicative of blood clotting or boiling, the microprocessor 42 sends a signal to the duty cycle generator 45 to reduce or discontinue the duty cycle of the power OUT1A, OUT1B and thus lower the effective power delivered to the band electrodes 32.

Similarly, the temperature at the electrodes 32 is determined by monitoring the power 14 and temperature signals 22 and measuring the voltage difference between the signals. As previously mentioned, in one embodiment of the invention, these signals pass through a filter 73 (FIG. 2-2) before being sent to the microprocessor 42. The voltage value is converted to a temperature and if the temperature is above a threshold level the duty cycle of the power 14 is reduced. In the case where a single lead is used to provide a signal which is used to determine the temperature as well as provide power to the electrode 32, the signal from the lead is received on temperature leads 87, 89 connected at the output side of the relays 88.

As shown in FIG. 3, the duty cycle of each electrode 32 may be individually controlled by the microprocessor 42. As previously mentioned, based on the temperature at an electrode 32 and the current and voltage of the output signal provided to an electrode, the duty cycle of the output signal may be adjusted. For example, one electrode 32 may have a temperature requiring a duty cycle of ten percent, while another electrode may have a temperature which allows for a fifty percent duty cycle. In an embodiment in which every other electrode 32 has a thermal sensor 40, the electrodes are grouped in pairs with each electrode in the pair having the same duty cycle.

In operation, as depicted in FIGS. 9A through 11D, the electrode device 16 and the backplate 24 are positioned proximal the biological site 26 undergoing ablation such that the biological site is interposed between the electrode device and the backplate. The band electrodes 32 (only one of which is indicated by a numeral 32 for clarity of illustration) of the electrode device 16 each receives power OUT1, OUT2, OUT3, OUT4 having a phase angle on LEAD 1 through LEAD 4. In one embodiment, every other electrode 32 receives the same phase angle. Therefore, the phase angle of electrode A equals the phase angle of electrode C and the phase angle of electrode B equals the phase angle of electrode D. The advantages of this arrangement are described below. In a preferred embodiment, the electrodes 32 are formed into a linear array as shown. In addition, a thermocouple thermal sensor 40 is located at each of the electrodes A, B, C, and D and uses the electrode power lead LEADS 1 through 4 as one of the sensor leads. The sensors 40 provide temperature sensor signals 22 for receipt by the power control system 12.

In another embodiment, alternate electrodes 32 may be grouped together and each may receive the same power having the same phase angle and duty cycle. Another group or groups of electrodes 32 may be interspaced with the first group such that the electrodes of one group alternate with the electrodes of the other group or groups. Each electrode 32 in a particular group of electrodes has the same phase angle and duty cycle. For example, electrodes A and C may be connected to the same power while interspaced electrodes B and D may be connected to a different power output signal.

The use of individual power signals also provides the ability to disable any combination of electrodes 32 and thereby effectively change the length of the electrode device 16. For example, in one configuration of the present invention an electrode device 16 with twelve electrodes 32 receives twelve power signals from a twelve channel power control system 12. The electrodes 32 are 3 mm in length and are 4 mm apart. Accordingly, by disabling various electrodes, a virtual electrode of any length from 3 mm to 8 cm may be produced by the electrode device 16. In either arrangement the backplate 24 is maintained at the reference voltage level in regard to the voltage level of the power OUT1 through OUTn.

As previously described, by varying the phase angles between the power OUT1, OUT2 supplied to each electrode 32, a phase angle difference is established between adjacent band electrodes. This phase angle difference may be adjusted to control the voltage potential between adjacent band electrodes 32 and thus to control the flow of current through the biological site 26. The flow of current $I_{e-e}$ between adjacent band electrodes 32 is defined by:

$$I_{e-e} = \frac{2V\sin\left(\frac{\Delta\Phi}{2}\right)\sin(2\pi ft)}{Z_{e-e}} \quad \text{(Eq. 2)}$$

where:
ΔΦ=phase angle difference between electrodes
V=voltage amplitude of power
$Z_{e-e}$=impedance between electrodes
f=frequency in hertz
t=time In addition to the current flow between the band electrodes 32 there is current flow between the band electrodes and the backplate 24. When the backplate 24 is set at the reference level, this current flow $I_{e-b}$ is defined by:

$$I_{e-b} = \frac{V\sin(2\pi ft)}{Z_{e-b}} \quad \text{(Eq. 3)}$$

where:
ΔΦ=phase angle difference between electrodes
V=voltage amplitude of power
$Z_{e-b}$=impedance between electrode and backplate
f=frequency in hertz
t=time Assuming $Z_{e-b}$ and $Z_{e-e}$ are equal, the ratio of the current flowing between the band electrodes 32 $I_{e-e}$ to the current flowing between the band electrodes 32 and the backplate 24 $I_{e-b}$ is defined by:

$$\frac{I_{e-e}}{I_{e-b}} = 2\sin\left(\frac{\Delta\Phi}{2}\right) \quad \text{(Eq. 4)}$$

where:
ΔΦ=phase angle difference between electrodes

FIGS. 9A through 11D illustrate various current flow patterns within a biological site. The depths and widths of the lesions depicted in FIGS. 9A through 11D are not necessarily to scale or in scalar proportion to each other but are provided for clarity in discerning the differences between the various power application techniques. When the phase difference between adjacent electrodes 32 is zero degrees, no current flows between the electrodes in accordance with Eq. 2 above, and the apparatus operates in a unipolar fashion with the current flowing to the backplate 24 as shown in FIGS. 9A through 9D. Substantially all current flows from the band electrodes 32 to the backplate 24 forming a series of relatively deep, acute lesions 90 along the length of the electrode device 16. As seen in the top view of FIG. 9B and the side view of FIG. 9D, the lesions are discrete. The lesions 90 are discontinuous in regard to each other.

Figure 10A:
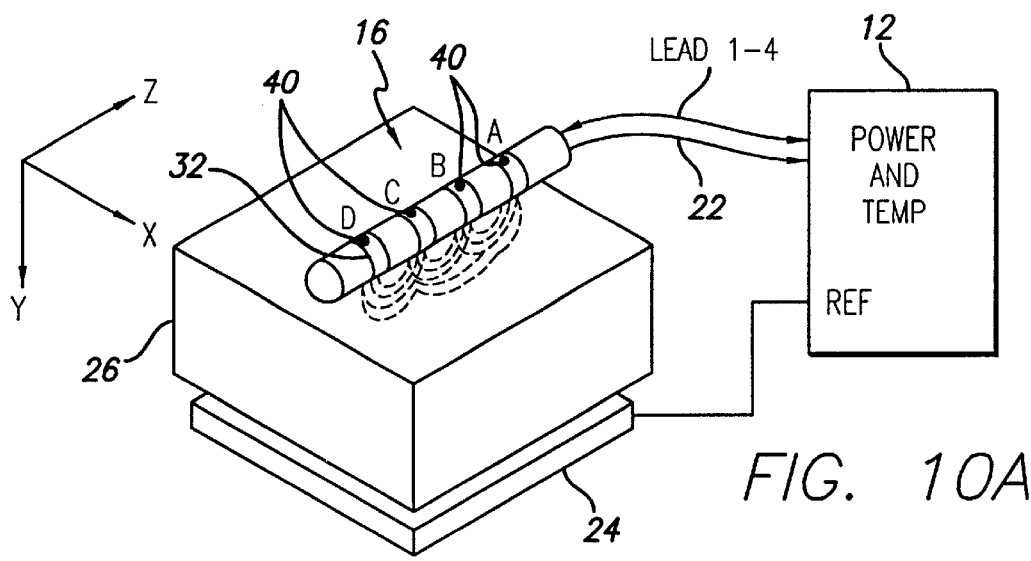
FIG. 10A is a three dimensional representation of an ablation apparatus having a linear array of band electrodes in contact with a biological site with a backplate at the opposite side of the biological site, in which the phase angle difference between adjacent electrodes is 180 degrees.
Figure 10B:
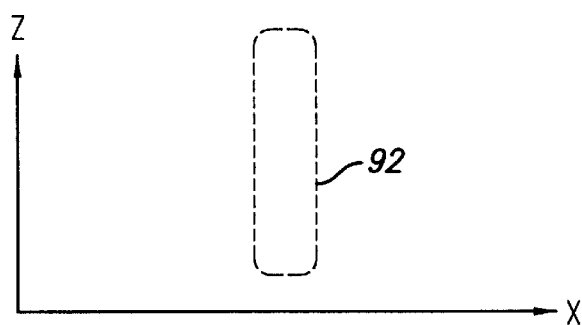
FIGS. 10B through 10D depict, along the x, y, and z axes shown, the continuity and depth of a lesion formed by the ablation apparatus of FIG. 10A showing that the apparatus acts as a bipolar device with no significant amount of current flowing to the backplate.
Figure 10C:
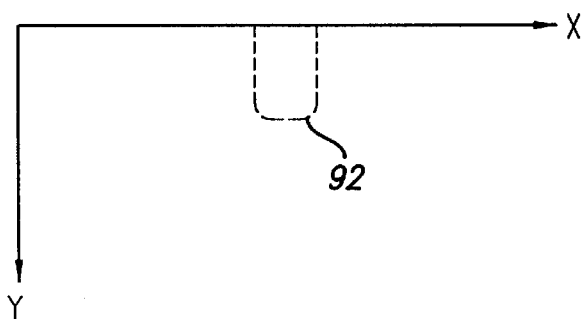
Figure 10D:
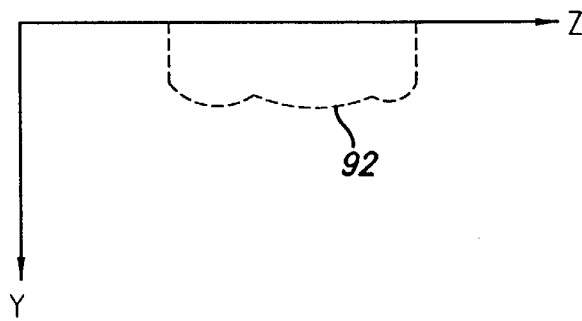

When the phase difference between adjacent electrodes 32 is 180 degrees the apparatus operates in both a unipolar and bipolar fashion and the current flow pattern is as shown in FIG. 10A. With this phase difference, approximately twice as much current flows between adjacent band electrodes 32 than flows from the band electrodes to the backplate 24. The resulting lesion 92 is shallow but is continuous along the length of the electrode device 16. The continuity and shallow depth of the lesion 92 are illustrated in FIGS. 10B through 10D. Nevertheless, the lesion depth is still greater than that created by prior bipolar ablation methods alone.

Figure 11A:
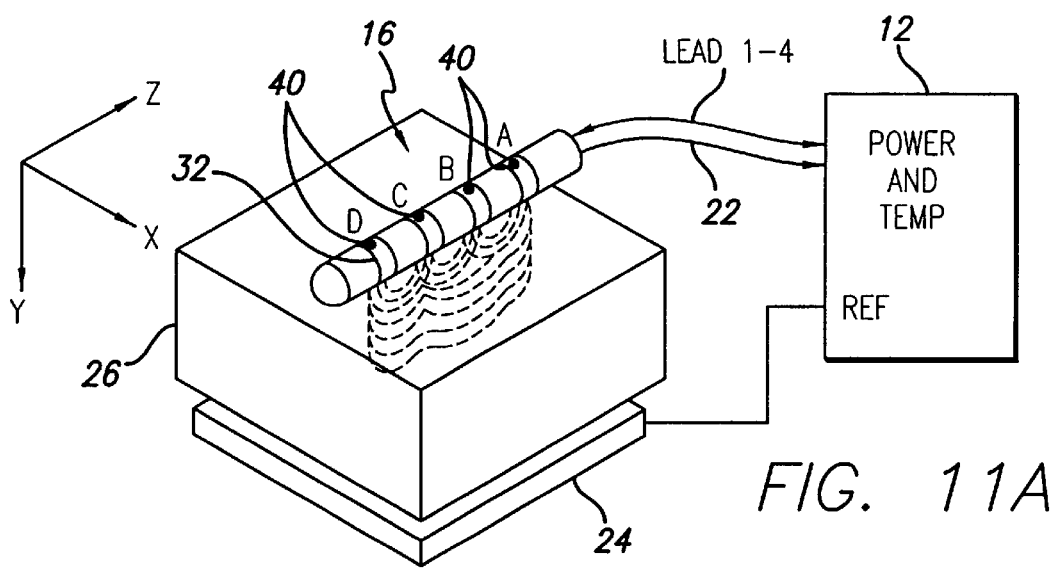
FIG. 11A is a three dimensional representation of an ablation apparatus having a linear array of band electrodes in contact with a biological site with a backplate at the opposite side of the biological site, in which the phase difference between adjacent electrodes is approximately 90 degrees.
Figure 11B:
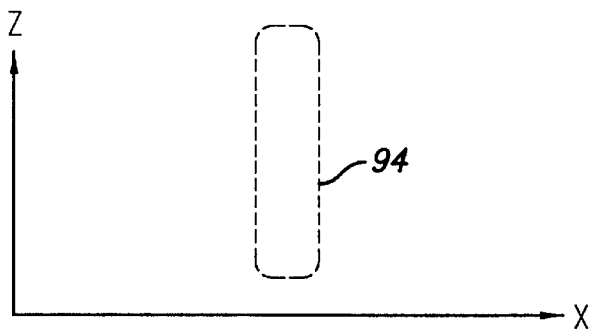
FIGS. 11B through 11D depict, along the x, y, and z axes shown, the continuity and depth of a lesion formed by the ablation apparatus of FIG. 11A showing the greater depth of lesion resulting from the phase angle difference.
Figure 11C:
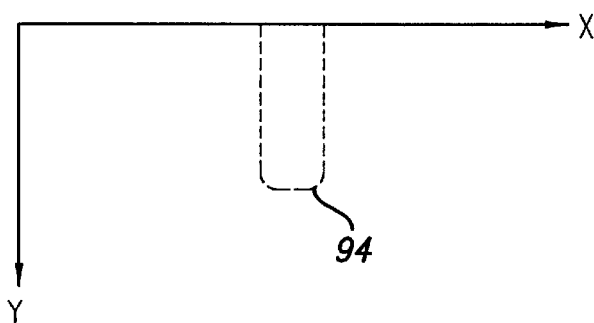
Figure 11D:
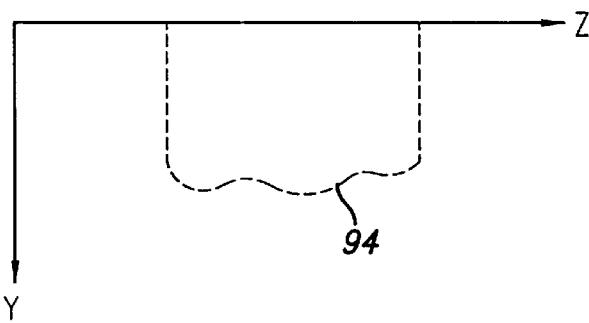

When the phase difference between adjacent electrodes 32 is set within the range of a value greater than zero to less than 180 degrees, the current flow varies from a deep, discontinuous unipolar pattern to a more continuous, shallow bipolar pattern. For example, when the phase difference between adjacent electrodes 32 is around 90 degrees, the current flows as shown in FIG. 11A. With this phase difference, current flows between adjacent band electrodes 32 as well as between the band electrodes and the backplate 24. Accordingly, a lesion which is both deep and continuous along the length of the electrode device 16 is produced. The continuity and depth of the lesion 94 is illustrated in FIGS. 11B through 11D. In one embodiment of FIG. 11A, adjacent electrodes alternated in phase but were provided with power in groups. Electrodes A and C were provided with power at a first phase angle and electrodes B and D were provided with power at a second phase angle, different from the first.

Thus, the phase angle of the power may be adjusted in order to produce a lesion having different depth and continuity characteristics. In selecting the phase angle difference necessary to produce a continuous lesion having the greatest possible depth, other elements of the electrode device 16 are considered. For example, the width of the band electrodes 32 and the spacing between the electrodes are factors in selecting an optimum phase angle. In a preferred embodiment of the present invention, as pointed out above, the width of the band electrodes is 3 mm, the spacing between the electrodes is 4 mm and the electrodes receive power which establish a phase difference of 132 degrees between adjacent electrodes. With this configuration a long continuous lesion having a length of between approximately 3 mm and 8 cm and a depth of 5 mm or greater was produced depending on the number of electrodes energized, the duty cycle employed, and the duration of power application.

In another embodiment, energy is applied to the biological tissue 26 during the on period of the duty cycle in an alternating unipolar-bipolar manner. During the unipolar mode segment a voltage potential is established between the electrodes 32 and the backplate 24. Thus current flows through the tissue 26 between the electrodes 32 and the backplate 24.

During the bipolar mode segment a voltage potential is established between at least two of the electrodes 32 rather than between the electrodes and the backplate 24. Thus current flows through the tissue 26 between the electrodes 32. While operating in this mode the voltage difference between the electrodes 32 may be established by providing power with different phase angles to the electrodes as previously mentioned. Alternatively, some of the electrodes 32 may be connected to a reference potential while others are maintained at a different voltage level.

By adjusting the duration of the unipolar and bipolar mode segments within the on period of the duty cycle, the continuity and depth of the lesion produced may be controlled. For example, operating in the unipolar mode for one-fourth of the on period and in the bipolar mode for three-fourths of the on period produces a lesion having a continuity and depth similar to the lesion 94 illustrated in FIGS. 11B through 11D.

Referring to FIGS. 8B through and 8E, the following devices are shown:

| Device | Part No. | Manufacturer |
|--------|----------|--------------|
| U1     | GAL6002B | Lattice      |
| U2     | SN75372  | numerous     |
| Q1     | 1RFZ34N  | numerous     |

-continued

| Device | Part No. | Manufacturer |
| --- | --- | --- |
| Q2, Q3, Q4, Q5 | 1RFZ44N | numerous |
| Q7, Q8, Q9 | MPF6601 | numerous |
| R3, R5 | 1Ω | numerous |
| T1, T4 | CMI-4810 | Corona Magnetics, Inc. |
| T2 | GFS97-0131-1 | GFS Manufacturing |
| T5 | CMI-4809 | Corona Magnetics, Inc. |

The transformer denoted by "T3" is a 1:12 turns ratio, single turn primary, step up transformer wound on a TDK core PC50EER23Z.

The band electrodes 32 generate a heating pattern in the tissue by transmitting RF power into the tissue. The power supplied to the band electrodes 32 is typically increased in order to increase the ablation volume until either an impedance change is noticed due to the onset of clotting or the temperature limit set for the electrode is reached. When one or both of these conditions exist the effective power delivered to the band electrodes 32 is reduced by reducing the duty cycle of the power signal in this embodiment.

Figure 13:
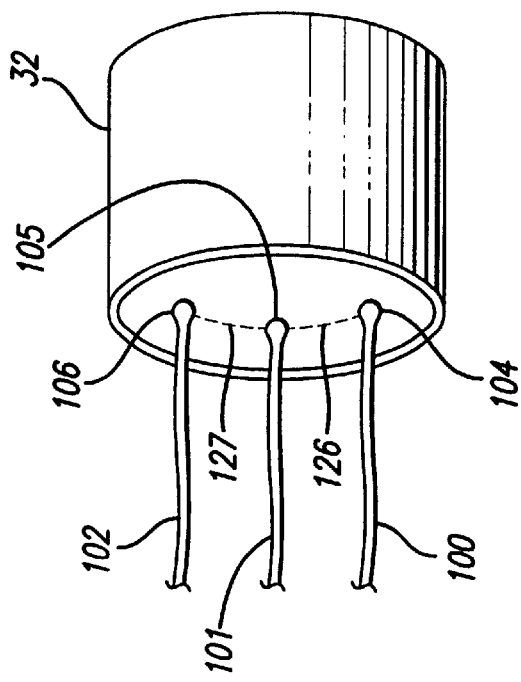
FIG. 13 is a diagram of a single band electrode showing the connection of two sensor thermocouple wires and a composition-matched, common-lead thermocouple wire.
Figure 12:
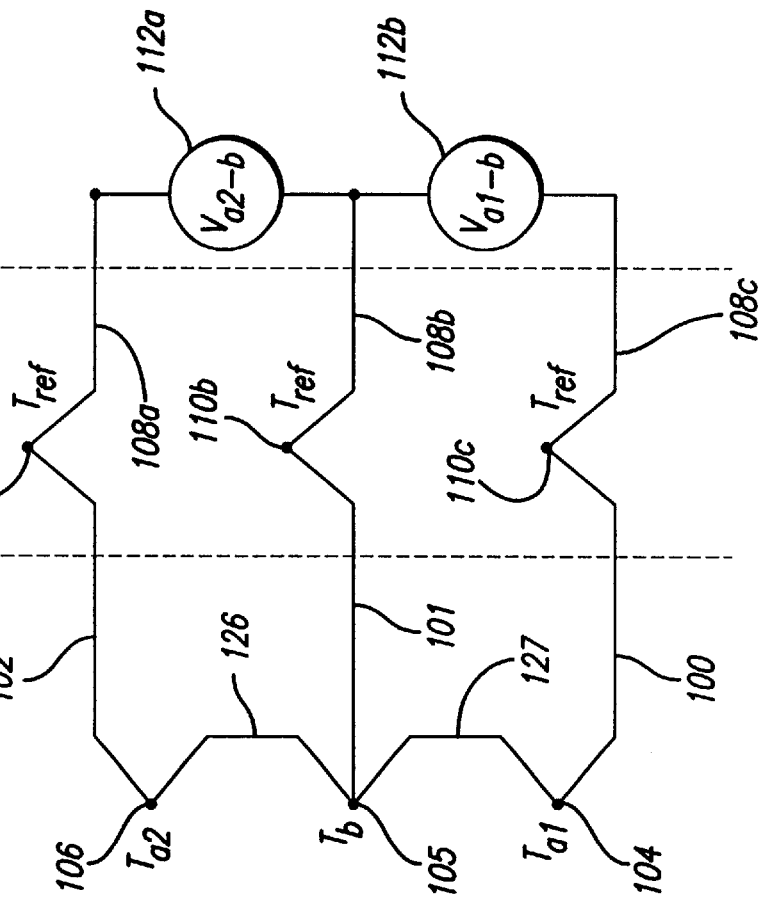
FIG. 12 is a schematic diagram of a thermocouple system having two sensor thermocouple wires and a composition-matched, common-lead thermocouple wire attached to a wire simulating a portion of a band electrode.

With reference to FIGS. 12 and 13, there is shown a electrode having two thermal sensors. First electrically conductive sensor lead 100, second electrically conductive sensor lead 102, and electrically conductive common lead 101 are connected independently to the band electrode 32 at two sensor junctions 104 and 106, and a common junction 105 respectively. Each of these junctions are separate from each other. These three electrically conductive members 100, 101, and 102 form the leads, i.e., or "legs" of what is essentially two thermocouples. Because of the separation between the locations at which the leads are attached to the inside surface of the band electrode, the portions 126 and 127 of the band electrode 32 between the connection points 104, 105, and 106 become part of the thermocouples and, in effect, serve as a large thermocouple bead. Associated with two of the junctions 104, 106 is a temperature-dependent voltage. This voltage is produced by the interface between two dissimilar metals and fluctuates in accordance with the temperature of the junction.

A conductive lead 108a, 108b, 108c is electrically connected to each sensor lead 100, 102 and the common lead 101 at a reference junction 110a, 110b, 110c. A voltmeter 112b is disposed across the conductive lead 108c connected to first sensor lead 100 and the conductive lead 108b connected to the common lead 101 to measure the temperature-dependent voltage developed in the thermocouple formed by sensor lead 100, common lead 101, and thermocouple bead 127. Similarly, a voltmeter 112a is disposed across the conductive lead 108a connected to second sensor lead 102 and the conductive lead 108b connected to the common lead 101 to measure the temperature-dependent voltage developed in the thermocouple formed by sensor lead 102, common lead 101, and thermocouple bead 126. In order to correct for extraneous voltage due to dissimilar metal junctions at the voltmeter terminals, the reference-junction lead 108 is preferably made of the same material as the first and second sensor leads 100 and 102. The reference junctions 110a, 110b, 110c and the leads 108a, 108b, 108c for use in connection to the voltmeters 112a, 112b are located in the handle 31 of the catheter and are therefore outside the patient. In another embodiment, the reference junctions 110a, 110b, 110c and conductive leads 108a, 108b, 108c are omitted and, as explained below, the reference temperature is assumed to be room temperature.

While FIGS. 12 and 13 depict only two sensor leads 100 and 102 it is possible to include a larger number of sensor leads positioned around the circumference of the band electrode 32. Each such sensor lead would form, in combination with the single common lead 101 and the thermocouple bead formed by the portion of the band electrode 32 between the sensor lead and common lead, a separate thermocouple. Each of these thermocouples provide a temperature-dependent voltage indicative of the temperature at the junction where the sensor lead is connected to the band electrode 32.

Conductive leads 100, 102, 108a, 108c are connected to voltmeters 112a, 112b located within the controller 20 (FIG. 1). A common lead 101, 108b is also connected to the voltmeters 112a, 112b. The voltmeters 112a, 112b (FIG. 12) provides voltage readings which are related to the temperatures at the various junctions 104, 105, 106, 110a, 110b, 110c. The resulting voltage output $V_{a1-b}$ measured by one of the voltmeters 112b is expressed by the following general equation:

$$V_{a1-b} = \alpha_{ac}(T_{a1} - T_{ref}) - \alpha_{bc}(T_b - T_{ref}) \quad \text{(Eq. 5a)}$$

where:

$\alpha_{ac}$=Seebeck coefficient for the first sensor lead 100 material and the band material $\alpha_{bc}$=Seebeck coefficient for the common lead 101 material and the band material $T_a$=temperature at the first sensor lead/electrode junction 104

$T_b$=temperature at the common lead/electrode junction 105

$T_{ref}$=temperature at the first sensor lead 100 reference junction 110c and the common lead reference junction 110b $T_{ref}$ and the two Seebeck coefficients, $\alpha_{ac}$ and $\alpha_{bc}$, are typically known for the system at hand.

The resulting voltage output $V_{a2-b}$ measured by the other voltmeter 112a is expressed by the following general equation:

$$V_{a2-b} = \alpha_{ac}(T_{a2} - T_{ref}) - \alpha_{bc}(T_b - T_{ref}) \quad \text{(Eq. 5b)}$$

where:

$\alpha_{bc}$ and $T_b$ are the same as described with reference to Eq. 5a $\alpha_{ac}$=Seebeck coefficient for the second sensor lead 102 material and the band material $T_{a2}$=temperature at the second sensor lead/electrode junction 106

$T_{ref}$=temperature at the second sensor lead 102 reference junction 110a and temperature at the common lead 101 reference junction 110b Again, the reference temperature $T_{ref}$ and the two Seebeck coefficients, $\alpha_{ac}$ and $\alpha_{bc}$, are typically known for the system at hand.

As mentioned briefly above, the reference junctions 110a, 110b, 110c are controlled temperature junctions which are normally included in order to correct for extraneous voltages due to dissimilar metal junctions at the voltmeter terminals. By being located in the handle, for example, the temperatures at these references are known to be room temperature, or approximately 22 degrees C. (72 degrees F). In addition, the Seebeck coefficients are assumed to be constant over the range of temperatures typically encountered in cardiac ablation.

The material of the common lead 101 is chosen such that the temperature-dependent voltage produced at the common junction 105 is substantially zero. This is preferably done by forming the common lead 101 of the same material as the band electrode 32 or alternatively by forming the common lead of a material having a thermoelectric output very similar to that of the band-electrode material. Thus the electrode 32 is described as having a "composition-matched" common lead 101. In one embodiment of the invention the band electrode 32 and the common lead 101 are formed of substantially pure platinum. In another embodiment, the band electrode 32 is formed of substantially pure platinum and the common lead is formed of a copper/nickel alloy containing approximately 1–2% nickel, which is known to those skilled in the art as "alloy 11." In addition to its platinum like thermoelectric properties, alloy 11 is also preferred because it is a low cost alternative to pure platinum leads. In either embodiment, $\alpha_{bc}$ approximately equals zero and Eq. 5a and Eq. 5b reduce to:

$$V_{a1-b} = \alpha_{ac}(T_{a1} - T_{ref}) \quad \text{(Eq. 6a)}$$

$$V_{a2-b} = \alpha_{ac}(T_{a2} - T_{ref}) \quad \text{(Eq. 6b)}$$

The materials of the first and second sensor leads 100, 102 are chosen such that the magnitude of the Seebeck coefficients of the materials relative to the band electrode 32 material is large. In order to increase the voltage output and improve temperature measurement resolution, preferably, the material of the first and second sensor leads 100, 102 is chosen such that the ratio of the magnitude of the Seebeck coefficient of the sensor lead 100, 102 material relative to the band electrode 32 material and the magnitude of the Seebeck coefficient of the common lead 101 material relative to the band electrode 32 is at least ten to one. In one preferred embodiment, the first and second sensor leads 100 and 102 were formed of constantan. Constantan is preferred because it has a large Seebeck coefficient relative to platinum and it is a commercially available alloy produced to tight thermoelectric property tolerances. These legs 100, 102 are connected to a band electrode 32 formed of substantially pure platinum. For pure platinum band electrodes 32, the following table provides approximate Seebeck coefficients (averaged over the temperature range of from zero to 100° C.) for a variety of different metals and alloys.

| METAL OR ALLOY | SEEBECK COEFFICIENT (mV/C) vs. PURE PLATINUM |
|---|---|
| Bismuth | −0.0734 |
| Constantan | −0.0351 |
| Nickel | −0.0148 |
| Cobalt | −0.0133 |
| Alumel | −0.0129 |
| Mercury | −0.0060 |
| Palladium | −0.0057 |
| Calcium | −0.0051 |
| Gold-chromium | −0.0017 |
| Thorium | −0.0013 |
| Platinum | 0 |
| Alloy 11 | +0.0013 |
| Tantalum | +0.0033 |
| Aluminum | +0.0042 |
| Tin | +0.0042 |
| Lead | +0.0044 |
| Magnesium | +0.0044 |
| Stainless steel, 18-8 | +0.0044 |
| Solder 96.5 Sn/3.5 Ag | +0.0045 |
| Solder 50 Sn/50 Pb | +0.0046 |

-continued

| METAL OR ALLOY | SEEBECK COEFFICIENT (mV/C) vs. PURE PLATINUM |
|---|---|
| Phosphor bronze | +0.0055 |
| Thallium | +0.0058 |
| Yellow brass | +0.0060 |
| Manganin | +0.0061 |
| Iridium | +0.0065 |
| Copper-beryllium | +0.0067 |
| Indium | +0.0069 |
| Rhodium | +0.0070 |
| Silver | +0.0074 |
| Copper | +0.0076 |
| Zinc | +0.0076 |
| Gold | +0.0078 |
| 60 Ni/24 Fe/16 Cr | +0.0085 |
| Cadmium | +0.0090 |
| Tungsten | +0.0112 |
| Cerium | +0.0114 |
| 80 Ni/20 Cr | +0.0114 |
| Spring steel | +0.0132 |
| Molybdenum | +0.0145 |
| Lithium | +0.0182 |
| Iron | +0.0189 |
| Chromel P | +0.0281 |
| Antimony | +0.0489 |

Thus, the arrangement shown in FIGS. 12 and 13 provides for multiple temperature-sensitive locations, i.e., junctions 104, 106, on the band electrode 32 using only three thermocouple wires 100, 101, 102, as opposed to two thermocouple pairs, i.e., four wires, thus resulting in a considerable saving of space in the ablation catheter.

In FIG. 13, a band electrode 32 is shown having a composition-matched common lead 101 and two sensor leads 100, 102 at the inside surface of the band. Each lead 100, 101 and 102 is separately connected to the band electrode 32 to form the three junctions 104, 105, and 106. Though the two sensor leads 100, 102 may be located anywhere on the band 32 they are preferably positioned approximately 60 degrees apart around the circumference of the band electrode. The common lead 101 may be positioned anywhere on the band electrode 32. In one embodiment (not shown) a separate power lead conducts power to the band electrode 32 to impart ablation energy to the biological target tissue. Thus four leads are used to provide power and to provide temperature sensing in two locations as opposed to five leads which would be required if each thermocouple had two leads.

In a preferred embodiment, the common lead 101 is also used to conduct power to the band electrode 32 to impart ablation energy to the biological target tissue. Thus, in the preferred embodiment only three leads 100, 101, 102 are used to provide power and to sense in two locations at the band electrode 32 rather than five leads as required by an electrode employing conventional thermocouples. This can result in a substantial savings in size because of the existence of fewer leads to be housed by the catheter. In the case of the twelve-band catheter described above in conjunction with FIG. 1, instead of sixty leads, which would be required with two thermocouples per band, each having two leads, and one power lead, only thirty-six leads are required. In a catheter having a thermal sensor on every other band electrode 32 only six of the electrodes require three leads while the remaining six require only one lead, for a total of only twenty-four leads. In a catheter having two sensors on six electrodes and one sensor on the remaining six, thirty leads are required. In any embodiment, there is a substantial decrease in the number of internal components for the catheter.

Because the thermocouple voltages are typically on the order of 0.001 mV to 0.10 mV per degree C., the power conducted on the common lead 101 could interfere with the detection of the temperature-dependent voltages generated at the sensor junctions 104, 106. Filtration could be used to separate the DC thermocouple signals from the drive or power signals. Such an arrangement is shown in FIG. 2.

In another approach, the controller 20 monitors the leads 100, 102 for thermocouple signals only during the off-period 76 of the duty cycle 78, for example, as shown in FIG. 6. During this off-period, no power is being applied to the band electrode 32 over the common electrode lead 101 and there is less chance for interference with the thermocouple signals produced by the band electrode 32 and conducted on both leads 100, 102. Thus, the temperatures may be measured briefly without electrical interference.

As shown in FIG. 14, an RF ablation catheter 120 is connected to an RF generator/controller 122. The catheter 120 includes a precurved distal region 124 which carries several band electrode 32. The catheter 120 is connected to the RF generator/controller 122 by interconnect cables 126. Backplates 24 are also connected to the RF generator/controller 122. The RF generator/controller 122 includes a display 128 for monitoring the temperatures provided by the thermal sensors 40 (not shown).

Figure 15:
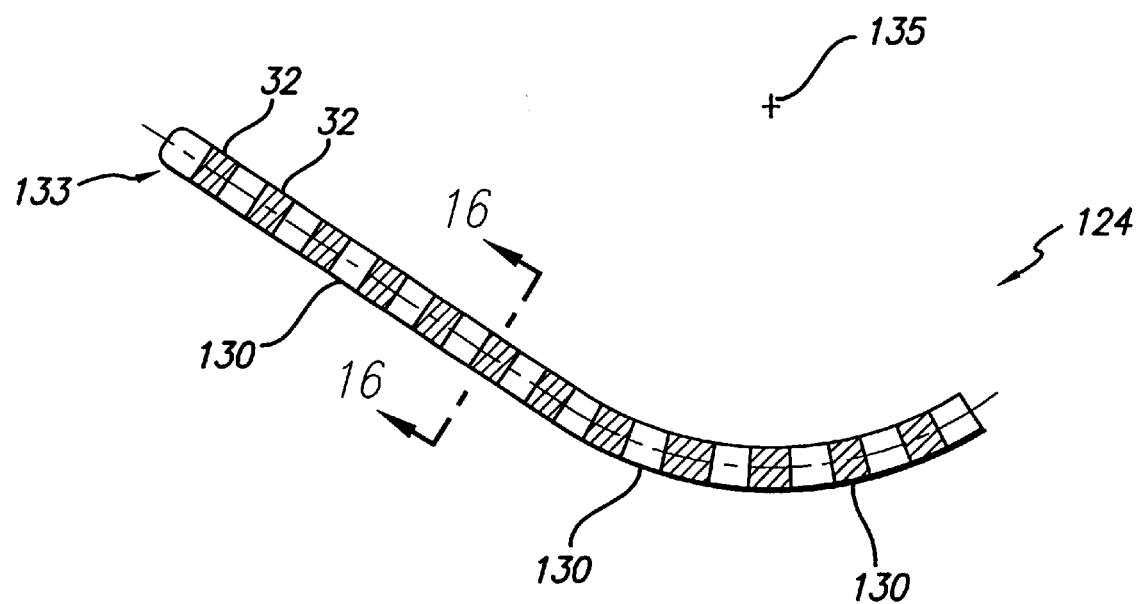
FIG. 15 depicts the distal end of the catheter of FIG. 14, including twelve spaced-apart band electrodes.
Figure 16:
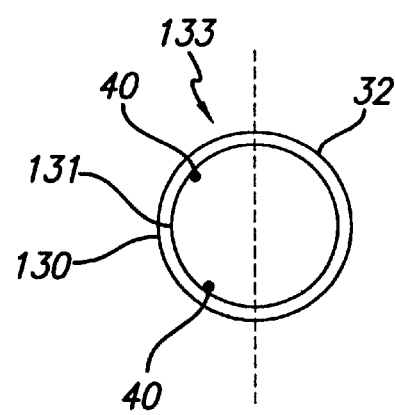
FIG. 16 is a cross-section view of the distal tip of FIG. 15 taken along line 16—16, depicting the position of two thermal sensors relative to the outside radius of curvature of the distal tip.

As shown in FIG. 15, the distal region 124 of the RF ablation catheter shown in FIG. 14, has an outside radius of curvature 130. The outside radius of curvature 130 is the longitudinal line positioned at the outer most point 131 of the outer half 133 of the catheter, most distant from a reference center point 135 of the catheter distal tip 124 curve. During ablation procedures, it is intended that the outside radius of curvature 130 contact the biological tissue undergoing ablation. As shown in FIG. 16, some of the band electrodes 32 may carry thermal sensors 40. In a preferred embodiment, there are twelve band electrodes 32, six of which carry two thermal sensors 40 affixed inside the band electrode. The two thermal sensors 40 are oriented near the catheter's outer radius of curvature 130, and are spaced approximately 60 degrees apart from each other, one on either side of the outside radius of curvature. This combination of at least two thermal sensors 40 and an electrode 32 is referred to herein as a "multiple-sensor" electrode.

In accordance with the present invention, electrode/thermal-sensor position assessment is provided by the combination of the thermal sensors 40 and the controller 20 (FIG. 1). The temperature readings from the sensors 40 are monitored by the controller 20 and displayed on a monitor associated with the controller. For each multiple-sensor electrode 32, the controller 20 monitors the magnitude of the difference between the temperatures of the sensors 40 associated with the electrode. The controller 20 is programmed to determine the "spread", i.e., the difference between the highest and lowest temperature readings, of each multiple-sensor electrode 32. Preferably, the magnitudes and the spread of each electrode 32 are displayed on the monitor. The display may be graphical or numeric or a combination of both. As shown in FIG. 17, for each multiple-sensor electrode 32 a spread 132 is created by plotting the temperatures of the two sensors 40 and connecting them with a bar. A short spread 132 means that both sensors 40 are at nearly the same temperature, whereas a longer spread 132 indicates that the two sensors 40 are at substantially different temperatures.

The display 128 includes a temperature range region 140 for displaying an upper temperature range, e.g., temperatures greater than approximately 60 degrees. Readings within this range are generally indicative of direct contact between at least one of the thermal sensors 40 and the tissue being ablated. The temperature range region 140 also includes a middle temperature range, e.g., temperatures between approximately 45 degrees and 60 degrees Celsius. Readings within this range are generally indicative of near contact between at least one of the thermal sensors 40 and the tissue being ablated. The temperature range region 140 further includes a lower temperature range, e.g., temperatures less than approximately 45 degrees Celsius. Readings within this range are generally indicative of no contact between the thermal sensors 40 and the tissue.

The display 128 also includes an electrode region 141 for displaying an electrode indicator, e.g., numbers 1 through 12, for each of the electrodes. The display 128 also includes a temperature data region 143 for displaying a graphic representation which correlates the temperature region 140 and the electrode region 141 to indicate the temperature of the thermal sensors associated with a particular electrode. The display 128 further includes power level displays 162 for displaying the power supplied to electrode groups. In the embodiment shown, the twelve electrodes are divided into three groups of four electrodes. Each electrode in the group is provided with the same power. In alternate embodiments of the system, each electrode 32 may have an individual power setting.

Figure 18A:
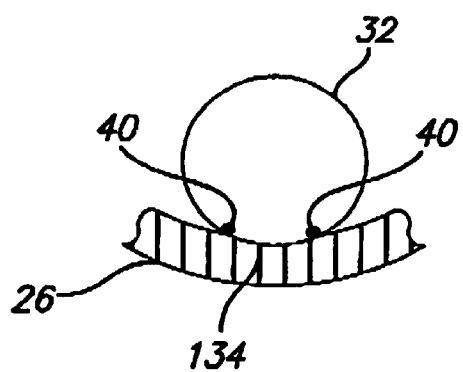
FIGS. 18a and 18b collectively depict a first scenario of thermal sensor/tissue positions in which at least one of the thermal sensors is directly on the electrode/tissue interface.

With reference to FIGS. 18a–20b, the relationship between the scenarios of electrode/thermal sensor 40 position relative to the tissue 26 and the spreads 132 (FIG. 17) displayed on the RF generator display 128 are now further described. It is significant to note that the power being applied to each electrode is substantially the same, e.g. 6 watts. Accordingly, the differences between the spreads 132 of the multiple-sensor electrodes, as described below, is due predominantly to thermocouple orientation differences. In the first scenario, as shown in the positions of FIGS. 18a and 18b, for the second and fourth electrodes respectively, at least one thermal sensor 40 is located directly over the electrode/tissue interface 134, thereby providing a reliable measurement of the interface temperature. On the display 128 (FIG. 17) these positions are indicated by spreads 136, 138 located in the upper region of the temperature range 140. The second-electrode spread 136 relates to the position of FIG. 18a. In this position, both sensors 40 are at the electrode/tissue interface 134. Accordingly, both sensors have substantially the same temperature and thus produce a short spread 136.

Figure 18B:
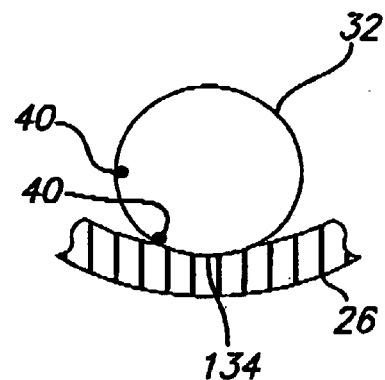

The fourth-electrode spread 138 relates to the position shown in FIG. 18b. In this position, only one of the sensors 40 is at the electrode/tissue interface 134 while the other sensor is in the local blood pool. Accordingly, the thermal sensor 40 at the interface 134 has a higher temperature. As such, the spread 138 produced is longer than the second-electrode spread 136.

In either position (FIG. 18a or 18b) of the first scenario, because of the proximity of the sensors 40 to the interface 134, any increase in the electrical energy applied to the electrode 32 produces a significant increase in the temperature sensed by the sensors. This increase in temperature is due to the additional generation of heat within the ablating tissue 26 that is conducted directly into the electrode 32 and the nearby sensors 40, through the interface 134.

Figure 19A:
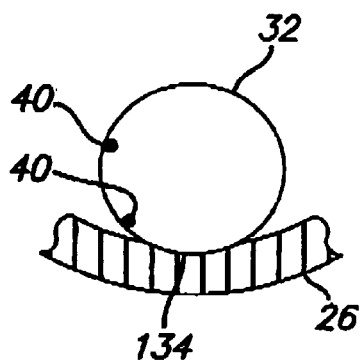
FIGS. 19a and 19b collectively depict a second scenario of thermal sensor/tissue positions in which neither of the thermal sensors is directly on the electrode/tissue interface but are close enough to sense an increase in temperature at the electrode/tissue interface.
Figure 19B:
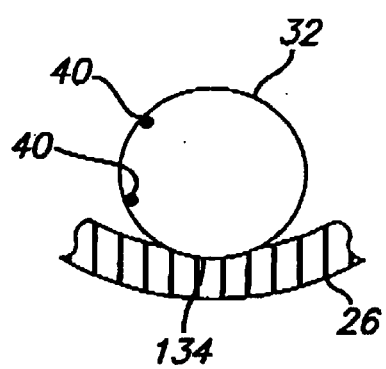

In the second scenario, as shown in the positions of FIGS. 19a and 19b, for the sixth and eighth electrodes respectively, none of the thermal sensors 40 are directly over the electrode/tissue interface 134, but the orientation of the electrodes 32 is adequate for at least one sensor to sense the heat generated at the interface. On the display 128 (FIG. 17) these positions are indicated by spreads 142, 144 located in the middle region of the temperature range 140. The sixth-electrode spread 142 relates to the position of FIG. 19a. In this position, neither thermal sensor 40 is at the electrode/ tissue interface 134, although one is substantially closer to the interface than the other. The thermal sensor 40 closer to the interface 134 is more sensitive to temperature increases at the interface while the sensor further within the blood pool is less sensitive to the interface temperature. This disparity in temperature sensitivity is due to the thermal gradient that exists around the perimeter of the electrode, wherein the highest temperatures occur at the electrode/tissue interface 134 and become cooler with increasing distance from the electrode/tissue interface. Thus the sensors 40 have substantially different temperatures and produce a long spread 142.

The eighth-electrode spread 144 relates to the position shown in FIG. 19b. In this position, both sensors 40 are further from the electrode/tissue interface 134 as compared to the position of FIG. 19a. Accordingly, both sensors 40 are less responsive to the temperature at the interface 134 and instead are more responsive to the cooling effect of the local blood pool. Because of this, the spread 144 associated with the eight-electrode sensors 40 tends to be short and toward the lower part of the middle region of the temperature range 140.

In either position (FIG. 19a or 19b) of the second scenario, any increase in the energy applied to an electrode 32 produces a less pronounced increase in the temperature sensed by the sensors 40 than in the first scenario (FIGS. 18a and 18b). Also, the size of the spread 142, 144 may be substantially different than in the first scenario, especially compared to the case in the first scenario where both sensors 40 are directly at the interface 134 (FIG. 18a).

Figure 20A:
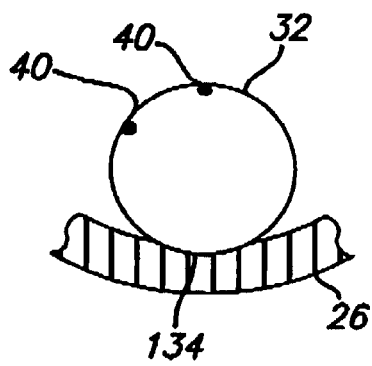
FIGS. 20a and 20b collectively depict a third scenario of thermal sensor/tissue positions in which neither of the thermal sensors is directly on the electrode/tissue interface and neither are close enough to sense an increase in temperature at the electrode/tissue interface.
Figure 20B:
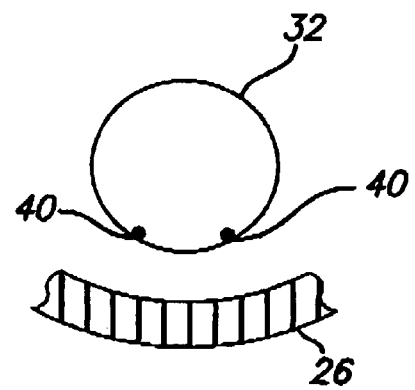

In the third scenario, as shown in FIGS. 20a and 20b, for the tenth and twelfth electrodes respectively, none of the thermal sensors 40 is directly over the electrode/tissue interface 134, and the orientation of the electrode is inadequate for any of the sensors to reliably sense the heat generated in the tissue 26 at the interface 134. On the display 128 (FIG. 17) these positions are indicated by spreads 146, 148 located in the lower region of the temperature range 140. The tenth-electrode spread 146 relates to the position of FIG. 20a. In this position, both sensors 40 are deep within the local blood pool and neither thermal sensor 40 is close enough to the electrode/tissue interface 134, to sense the heat generated in the tissue 26. While the thermal sensor 40 closer to the interface 134 is more sensitive to temperature increases at the interface than the other sensor, it is too far in the blood pool to be adequately responsive to increasing interface temperatures. Thus the sensors 40 have close temperatures more indicative of the blood-pool temperature than the interface 134 temperature and accordingly produce a short spread 146.

The twelfth-electrode spread 148 relates to the position shown in FIG. 20b. In this position, the electrode 32 does not contact the tissue 26 and both sensors 40 are within the local blood pool. Accordingly, both sensors 40 are only responsive to the cooling effect of the local blood pool and are thus substantially at the same temperature. Because of this, the spread 148 associated with the twelfth-electrode sensors 40 tends to be short and toward the lower part of the lower region of the temperature range 140.

In either position (FIG. 20a or 20b) of the third scenario, any increase in the energy applied to an electrode 32 produces a negligible increase in the temperature sensed by the sensors 40. Thus the temperature response as the energy applied to the electrode 32 is increased is negligible and the spread 146, 148 is small.

In operation, the known location of the sensors 40 on the multiple-sensor electrode 32 with respect to each other and with respect to the outside radius of curvature of the catheter, in combination with the display of the temperatures sensed by each sensor, is used to facilitate decisions regarding the steering of the catheter and the application of electrical energy to the catheter electrodes. Decisions regarding catheter steering are performed manually in that the system user, in view of the display, determines what steering, if any, is necessary in order to properly position the catheter electrode 32 for ablation. Decisions regarding the application of energy may be performed manually, in view of the display, or automatically by the controller 20.

At the start of an ablation procedure, the application of power to each electrode 32 is controlled by the controller 20 as follows: Initially, the controller 20 causes the power generator 18 to apply power of an initial level to each electrode 32. The controller 20 maintains the power level to each electrode at this initial level. When one of the temperature sensors 40 returns a temperature sufficient to cause ablation, i.e., an ablation temperature, to the controller 20, the controller reduces the initial power level to that electrode 32 to a subsequent power level sufficient to maintain the highest temperature signal for that electrode at or near the ablation temperature. In one embodiment of the system, the procedure is conducted individually for each electrode 32. In an alternate operation, the controller 20 incrementally increases the initial power level to each electrode 32 in order to reach the ablation temperature sooner. Again, once the ablation temperature is reached, the controller 20 reduces the power level to maintain the highest sensor temperature at or near the ablation temperature.

Assuming that the blood flow conditions and the local cooling effect are the same for each electrode and further assuming that the level and duration of energy applied to each electrode is also the same, the display of FIG. 21 indicates the following:

With regard to electrodes #2 and #4, the location of their spreads 150, 152 in the lower region of the temperature range 140 is indicative of the positions in FIGS. 20a and 20b. In this situation, increasing the applied electrical energy is not recommended. Instead, it is recommended that the catheter be repositioned to ensure that the electrode 32 contacts the tissue and that the ablation therapy be repeated in the vicinity of electrodes #2 and #4. Note that from these spreads 150, 152 it is not possible to determine whether electrodes #2 and #4 are actually making tissue contact, so the prudent decision for both electrodes #2 and #4 is to repeat therapy.

With regard to electrodes #6 and #8, the location of their spreads 154, 156 in the upper region of the temperature range 140 is indicative of the positions in FIGS. 18a and 18b. Given this, increasing the applied electrical energy to electrodes #6 and #8 is not necessary, since the electrode/tissue interface temperature is within a desirable range. Instead, the applied electrical energy should only be adjusted to maintain the present temperature.

With regard to electrodes #10 and #12, the location of their spreads 158, 160 in the middle region of the temperature range 140 is indicative of the positions shown in FIGS. 19a and 19b. It is noted that if only the highest sensor reading from each of the electrodes is displayed, it may be tempting to increase the applied energy to electrodes #10 and #12 in order to force the temperature readings to appear more like those of electrodes #6 and #8. However, since the sensors 40 on electrodes #10 and #12 are not directly upon the electrode/tissue interface 134, raising the applied energy is not recommended due to the risk of overheating the electrode/tissue interface and/or forming coagulum. Instead, it is recommended that the applied energy levels for electrodes #10 and #12 be maintained at levels comparable to #6 and #8, even though their upper display temperatures are different.

It should be emphasized here that the additional information provided by displaying all sensor temperatures does not unequivocally distinguish among the three scenarios. However, conveniently displaying this information is expected in most cases to help the user to decide which scenario is most probable for the clinical conditions at hand and to thus make applied energy adjustments with greater insight.

To further assist in the assessment of electrode 32 and thermal sensor 40 position and applied energy levels, the controller 20 may be programmed to store a threshold spread value and to provide position indications and power level adjustments in view of measured spreads relative to the threshold spread. The threshold spread value is generally the value at which continued application of power to an electrode 32 at its present level is likely to produce coagulum in the fluid in the biological site. For example, for an electrode 32 positioned in blood and having 8 watts of power applied, the threshold value is likely to be around 5° Celsius.

Figure 22:
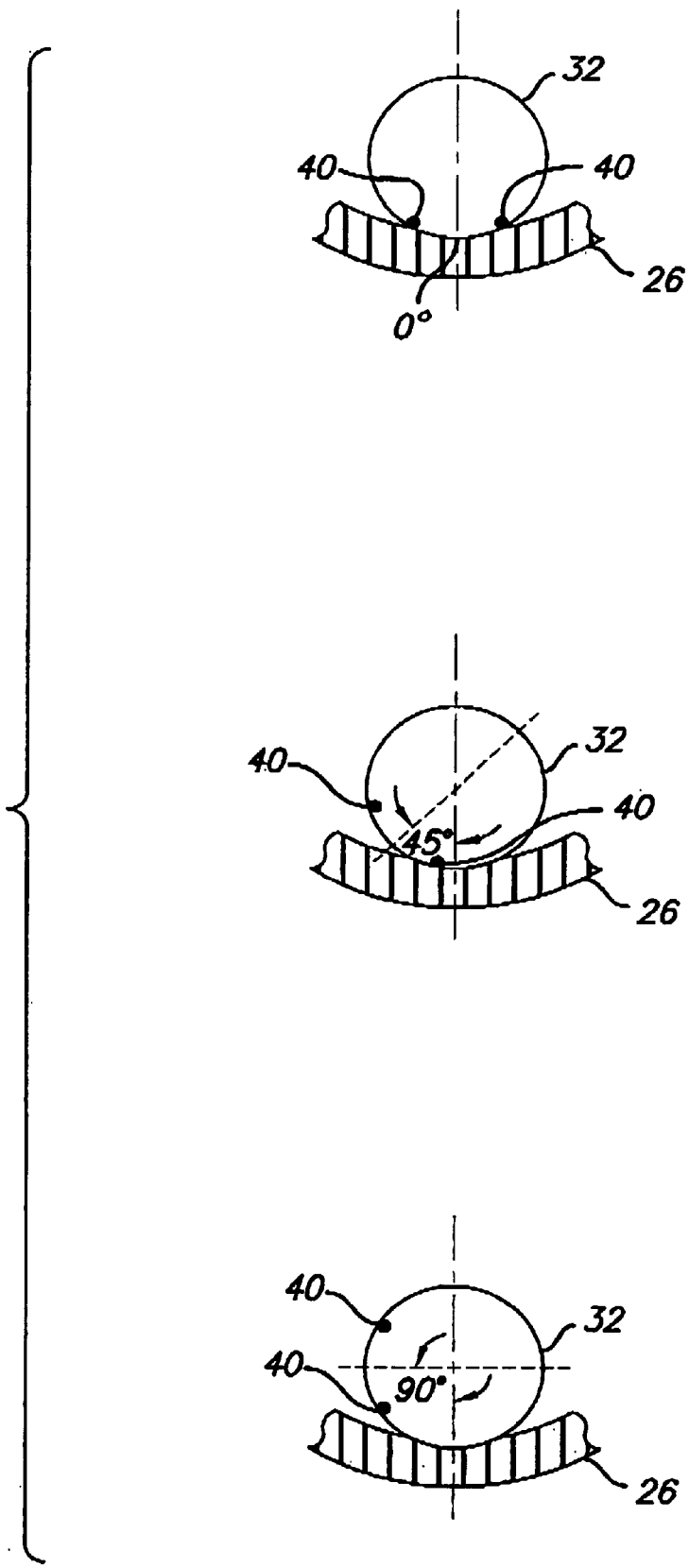
FIG. 22 depicts various positions of a multiple-sensor electrode relative to biological tissue.

Experimentation has shown that a correlation exists between the spread of a multiple-sensor electrode 32 and the position of the sensors 40 relative to the biological tissue being ablated. The following table lists the average spreads measured for an electrode positioned at 0°, 45° and 90° rotations, relative to the tissue, as shown in FIG. 22. Under experimental conditions, eight watts of energy was applied to each of a plurality of electrodes as their hotter sensor values gradually reached the indicated target temperature, e.g. 47°, 57°, 67°, and 77°. Each electrode's spread when it first reached the indicated target temperature was then calculated. As shown in the following table of average spread values, greater spreads tend to be associated with rotated or "misoriented" electrodes, especially as the target temperature increases. Conversely, properly oriented electrodes tend to have relatively small spread values, regardless of target temperature.

| Target temp. C. | 0° rotation | 45° rotation | 90° rotation |
|---|---|---|---|
| 47° | 0.5 | 1.6 | 2.4 |
| 57° | 0.9 | 3.2 | 5.5 |
| 67° | 1.6 | 5.7 | 9.2 |
| 77° | 1.8 | 8.0 | 12.0 |

In order to avoid coagulum forming conditions, it is necessary that the electrode 32 be properly oriented, i.e., positioned against the tissue with the sensors 40 at or near the electrode/tissue interface, in order to provide accurate tissue temperature readings. Under certain conditions a misoriented electrode may not cause coagulum. For example, when the highest temperature of the electrode is only 47°, coagulum will probably not form, regardless of the electrode's orientation. However, as the highest electrode temperature increases toward 67° and 77°, the probability that a misoriented electrode will form coagulum increases. Based on the above data, the system would likely set its threshold spread value to about 5. The invention is in no way limited by the above, exemplary data. Depending on a particular biological site, different threshold spread values may be appropriate.

The controller 20 may be programmed to provide an enhanced display indication when a particular electrode spread exceeds the threshold spread value. The indication may be, for example, an alternate illumination, backlighting or flashing number indicative of the "offending" electrode. As used herein an offending electrode is an electrode having a spread that exceeds the threshold spread value. This enhanced indication assists the system user by identifying electrodes 32 which may be positioned poorly and have inadequate electrode/tissue contact. In the presence of such an indication the user may manually adjust the power level being applied to the electrode 32 in order to reduce the actual electrode/tissue interface temperature and thus the possibility of producing coagulum.

In the automatic mode of operation, the user is presented the same display as in the manual mode, however, certain decisions regarding the application of energy to the electrodes 32 are made by the controller 20. In one embodiment of the system, the power level applied to an offending electrode 32 is automatically lowered by the controller 20. For example, if the threshold spread is 5 and an electrode 32 having 8 watts of power applied has a spread larger than 5, the power level may be reduced to a value less than 8 watts. Alternatively, the power level applied to an offending electrode may be incrementally reduced to any one of a plurality of subsequent lower power levels until the spread is less than the threshold value. In an ablation system having a plurality of multiple-sensor electrodes, the subsequent, lower power level applied to an offending electrode may be set to a power level equal to that of a nonoffending electrode within the system. Alternatively, the power to the offending electrode may be automatically shut off.

In an alternate embodiment of the system, one or more electrodes 32 may be grouped in an electrode zone. For example, for a catheter with twelve electrodes, there may be four zones, each with three electrodes, or six zones each with two electrodes or any other combination. At least one of the electrodes 32 in each zone is a multiple-sensor electrode. The spreads of the multiple-sensor electrodes are monitored to identify offending electrodes. The power to each electrode 32 within the electrode zone of any identified offending electrode is either shut off or reduced to a level sufficient to reduce the spread of the offending electrode to a value less than the threshold value.

In another automatic mode of operation, during an ablation procedure using a catheter having a plurality of multiple-sensor electrodes, the controller 20 monitors the temperatures of each sensor 40 to first identify those multiple-sensor electrodes having at least one temperature at a "target" temperature, i.e., a temperature sufficient to cause ablation of the given biological site. For each electrode 32 having a sensor temperature at the target temperature, the controller 20 monitors the spread associated with the electrode to identify those electrodes having a spread less than the spread threshold value. The controller then compares the power levels of each of the electrodes 32 identified as having both reached the target temperature and having a spread less than the spread threshold value to identify the electrode 32 having the lowest power level applied to it. In view of it having reached the target temperature at the lowest power rating and further in view of it having nonoffending spread, the identified electrode is likely to be making good tissue contact with its thermal sensors oriented favorably with respect to the electrode/tissue interface. As such, the identified electrode is not likely to experience coagulum. The controller 20 then sets the power level to each of the electrodes 32 to a power level substantially equal to the power level being applied to the identified electrode. In setting the power level of the other electrodes 32 as such, they become less likely to experience coagulum.

It should be appreciated that the invention may also be applied to ablation catheters employing alternate sources of energy for ablation, such as ultrasound or microwave energy. The invention may also be applied to any system in which monitoring temperature is important and where the position of thermal sensors is important to the monitoring process.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An apparatus for controlling the application of energy to biological tissue during an ablation procedure using an electrode having at least two thermal sensors attached at separate points thereto for providing temperature signals indicative of the temperatures of the electrode at the attachment points, said apparatus comprising:
    a generator for applying power to the electrode; and
    a processor programmed to:
       store a spread threshold value,
       monitor the spread between the temperatures of the at least two thermal sensors, and
       cause the generator to reduce the power applied by the generator when the spread exceeds the threshold value.

2. The apparatus of claim 1 wherein the processor is further programmed to:
    store an ablation temperature;
    apply power of an initial level to the electrode;
    maintain the initial power level until at least one of the temperature signals reaches the ablation temperature; and
    reduce the initial power level to a subsequent power level to maintain the at least one temperature signal at the ablation temperature.

3. The apparatus of claim 1 wherein the processor is further programmed to:
    store an ablation temperature;
    apply power of an initial level to the electrode;
    increase the initial power level to a subsequent power level until at least one of the temperature signals reaches the ablation temperature; and
    reduce the subsequent power level to another subsequent power level to maintain the at least one temperature signal at the ablation temperature.

4. The apparatus of claim 1 wherein the processor is further programmed to set the power to substantially zero when the spread exceeds the threshold value.

5. The apparatus of claim 1 wherein the processor is further programmed to reduce the power until the spread is less than the threshold when the spread begins to exceeds the threshold value.

6. In a biological tissue ablation procedure using a catheter comprising a plurality of electrodes, at least two of the electrodes being multiple-sensor electrodes having at least two thermal sensors attached at separate points thereto for providing temperature signals indicative of the temperatures of the electrode at the points of attachment, an apparatus for controlling the application of energy to the biological tissue comprising:
    a generator operating under the control of a processor to apply power to each multiple-sensor electrode,
    wherein the processor is programmed to:
       for each multiple-sensor electrode, monitor the spread between the temperatures of the at least two thermal sensors associated with the multiple-sensor electrode; and
       if any one of the spreads exceeds a spread threshold value, cause the generator to reduce the power to at least the multiple-sensor electrode associated with that spread.

7. The apparatus of claim 6 wherein when any one of the spreads exceeds the threshold value the processor is further programmed to cause the generator to set the power to the multiple-sensor electrode associated with that spread to substantially zero.

8. The apparatus of claim 6 wherein the catheter comprises a plurality of electrode zones each comprising at least one multiple-sensor electrode and when any one of the spreads exceeds the threshold value the processor is further programmed to cause the generator to set the power to each of the electrodes within the electrode zone associated with that spread to substantially zero.

9. The apparatus of claim 6 wherein when any one of the spread exceeds the threshold value the processor is further programmed to cause the generator to reduce the power to the multiple-sensor electrode associated with that spread until the spread is less than the threshold.

10. The apparatus of claim 6 wherein the catheter comprises a plurality of electrode zones each comprising at least one multiple-sensor electrode and when any one of the spreads exceeds the threshold value the processor is further programmed to cause the generator to reduce the power to each of the electrodes within the electrode zone associated with that spread until the spread is less than the threshold.

11. The apparatus of claim 6 wherein when any one of the spread exceeds the threshold value, the processor is further programmed to:
    monitor the spread of each of the other multiple-sensor electrodes and the power levels associated therewith; and
    if any one of the spreads is acceptable, cause the generator to set the power to the multiple-sensor electrode associated with the excessive spread to a power level substantially equal to any one of the power levels associated with any one of the acceptable spreads.

12. The apparatus of claim 6 wherein the catheter comprises a plurality of electrode zones each comprising at least one multiple-sensor electrode and when any one of the spreads exceeds the threshold value, the processor is further programmed to:
    monitor the spread of each of the other multiple-sensor electrodes and the power levels associated therewith; and
    if any one of the spreads is acceptable, cause the generator to set the power to each of the electrodes within the electrode zone associated with the excessive spread to a power level substantially equal to any one of the power levels associated with any one of the acceptable spreads.

13. In a biological tissue ablation procedure using a catheter comprising a plurality of electrodes, at least two of the electrodes being multiple-sensor electrodes having two thermal sensors attached at separate points thereto for providing temperature signals indicative of the temperatures of the electrode at the points or attachment, an apparatus for controlling the application of energy to the biological tissue comprising:

a generator operating under the control of a processor to apply power to each multiple-sensor electrode, wherein the processor is programmed to:

store a target temperature and a spread threshold;

for each multiple-sensor electrode, monitor the temperatures of each sensor to first identify those electrodes having at least one temperature that is at least as great as the target temperature;

for each first identified electrode, monitor the spread between the temperature of the two thermal sensors to second identify those electrodes having a spread less than the spread threshold;

compare the power levels of each of the second identified electrodes to third identify the electrode having the lowest power level; and cause the generator to set the power level to each of the multiple-sensor electrodes to a power level substantially equal to the power level of the third identified electrode.

* * * * *

UNITED STATES PATENT AND TRADEMARK OFFICE
CERTIFICATE OF CORRECTION

PATENT NO.   : 6,752,804 B2
DATED        : June 22, 2004
INVENTOR(S)  : John A. Simpson et al.

It is certified that error appears in the above-identified patent and that said Letters Patent is hereby corrected as shown below:

Column 17,
Line 23, delete "a" and insert -- an --.

Column 27,
Line 58, delete "exceeds" and insert -- exceed --.

Column 28,
Line 65, delete "or" and insert -- of --.

Signed and Sealed this

Twenty-fifth Day of January, 2005

JON W. DUDAS
*Director of the United States Patent and Trademark Office*

UNITED STATES PATENT AND TRADEMARK OFFICE
CERTIFICATE OF CORRECTION

PATENT NO. : 6,752,804 B2
DATED : June 22, 2004
INVENTOR(S) : John A. Simpson et al.

It is certified that error appears in the above-identified patent and that said Letters Patent is hereby corrected as shown below:

Column 17,
Line 23, delete "a" and insert -- an --.

Column 27,
Line 58, delete "exceeds" and insert -- exceed --.

Column 28,
Line 65, delete "or" and insert -- of --.

Signed and Sealed this

Twenty-fifth Day of January, 2005

JON W. DUDAS
*Director of the United States Patent and Trademark Office*